(12) United States Patent
Berg

(10) Patent No.: US 11,537,731 B2
(45) Date of Patent: *Dec. 27, 2022

(54) RECEIVING CONTENT PRIOR TO REGISTRATION OF A SENDER

(71) Applicant: MyMedicalImages.com, LLC, Boca Raton, FL (US)

(72) Inventor: Troy Berg, La Crosse, WI (US)

(73) Assignee: MYMEDICALIMAGES.COM, LLC, Boca Raton, FL (US)

( * ) Notice: Subject to any disclaimer, the term of this patent is extended or adjusted under 35 U.S.C. 154(b) by 247 days.

This patent is subject to a terminal disclaimer.

(21) Appl. No.: 17/014,328

(22) Filed: Sep. 8, 2020

(65) Prior Publication Data
US 2020/0401713 A1 Dec. 24, 2020

Related U.S. Application Data

(63) Continuation of application No. 16/115,295, filed on Aug. 28, 2018, now Pat. No. 10,796,010.
(Continued)

(51) Int. Cl.
| | |
|---|---|
| *H04L 9/40* | (2022.01) |
| *G06F 21/62* | (2013.01) |
| *G16H 30/20* | (2018.01) |
| *G06F 16/955* | (2019.01) |
| *H04L 9/32* | (2006.01) |

(Continued)

(52) U.S. Cl.
CPC .......... *G06F 21/6209* (2013.01); *G06F 16/58* (2019.01); *G06F 16/9558* (2019.01); *G06F 16/9566* (2019.01); *G16H 30/20* (2018.01); *H04L 9/3239* (2013.01); *H04L 9/50* (2022.05); *H04L 63/0227* (2013.01); *H04L 63/102* (2013.01); *H04L 67/02* (2013.01)

(58) Field of Classification Search
CPC ............. G06F 21/6209; G06F 16/9558; G06F 16/9566; G06F 16/58; G16H 30/20; H04L 9/3239; H04L 63/0227; H04L 63/102; H04L 67/02; H04L 2209/38; H04L 9/50
See application file for complete search history.

(56) References Cited

U.S. PATENT DOCUMENTS 7,116,807 B1    10/2006    Brackett
8,255,686 B1 *    8/2012    Sharma ............... H04L 63/0428
                                                                                                                            713/153

(Continued)

OTHER PUBLICATIONS

Official Action dated May 18, 2022 in EP Application No. 18850131.6.

(Continued)

*Primary Examiner* — Ghodrat Jamshidi
(74) *Attorney, Agent, or Firm* — Snell & Wilmer L.L.P.

(57) ABSTRACT

The system may include a method comprising requesting, by a computer, a receiver identifier associated with a receiver; receiving, by the computer, the receiver identifier in association with content; constructing, by the computer, a URL link comprising access to DICOM viewer code, DICOM data for the selected images, a sender identifier and the receiver identifier; generating, by the computer, a notification to the receiver, wherein the notification includes the URL link; and transmitting, by the computer, the notification to a receiver based on the receiver identifier.

20 Claims, 27 Drawing Sheets

Related U.S. Application Data

(60) Provisional application No. 62/552,373, filed on Aug. 30, 2017.

(51) Int. Cl.
    *G06F 16/58*     (2019.01)
    *H04L 67/02*     (2022.01)
    *H04L 9/00*     (2022.01)

(56) References Cited

U.S. PATENT DOCUMENTS

| | | | |
|---|---|---|---|
| 8,331,251 B2 * | 12/2012 | Suzuki | H04L 63/1425 370/395.31 |
| 8,756,437 B2 | 6/2014 | Monk | |
| 2002/0016718 A1 | 2/2002 | Rothschild et al. | |
| 2003/0167405 A1 | 9/2003 | Freund et al. | |
| 2004/0255048 A1 | 12/2004 | Lev Ran et al. | |
| 2005/0066018 A1 | 3/2005 | Whittle et al. | |
| 2005/0111733 A1 | 5/2005 | Fors et al. | |
| 2005/0216314 A1 | 9/2005 | Secor | |
| 2006/0007868 A1 | 1/2006 | Shinomiya | |
| 2009/0012968 A1 * | 1/2009 | Hayashi | G16H 30/20 382/128 |
| 2009/0271506 A1 * | 10/2009 | Arai | H04L 67/1097 709/223 |
| 2010/0122336 A1 * | 5/2010 | Hunt | H04L 67/55 726/11 |
| 2011/0153351 A1 | 6/2011 | Vesper et al. | |
| 2011/0191767 A1 | 8/2011 | Pinsky et al. | |
| 2011/0302268 A1 | 12/2011 | Fimreite | |
| 2012/0022885 A1 * | 1/2012 | Murayama | G16H 20/00 705/2 |
| 2013/0086636 A1 * | 4/2013 | Golovanov | G06F 21/56 726/3 |
| 2014/0114672 A1 * | 4/2014 | Wright | G16H 30/20 705/2 |
| 2014/0156630 A1 | 6/2014 | Yin et al. | |
| 2015/0120326 A1 * | 4/2015 | Atanasiu | G16Z 99/00 705/3 |
| 2015/0331872 A1 | 11/2015 | Westin et al. | |
| 2016/0197849 A1 * | 7/2016 | Self | H04L 51/066 709/228 |
| 2016/0212079 A1 | 7/2016 | Oliver et al. | |
| 2017/0076043 A1 * | 3/2017 | Dormer | G16H 40/67 |
| 2017/0208047 A1 | 7/2017 | Rosenberg | |
| 2017/0329473 A1 * | 11/2017 | Barger | G06F 16/22 |

OTHER PUBLICATIONS

Notice of Allowance dated Jul. 28, 2022 in Canadian Application No. 3074266.

International Search Report and Written Opinion dated Feb. 7, 2019 in PCT application No. PCT/US2018/048520.

USPTO, Non-Final Office Action dated Apr. 16, 2020 in U.S. Appl. No. 16/115,295.

USPTO, Final Office Action dated May 8, 2020 in U.S. Appl. No. 16/115,295.

USPTO, Notice of Allowance dated Jun. 11, 2020 in U.S. Appl. No. 16/115,295.

* cited by examiner

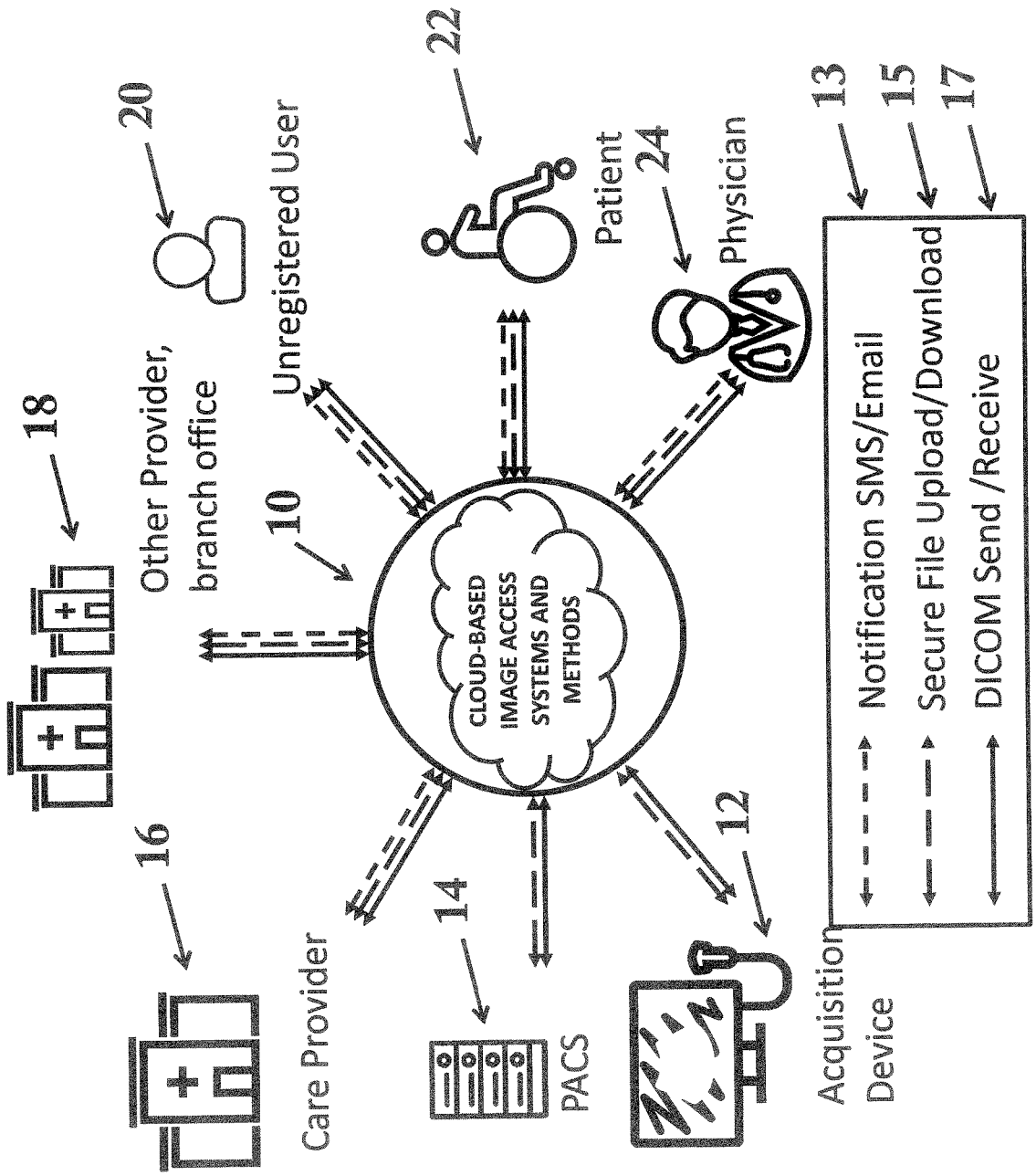

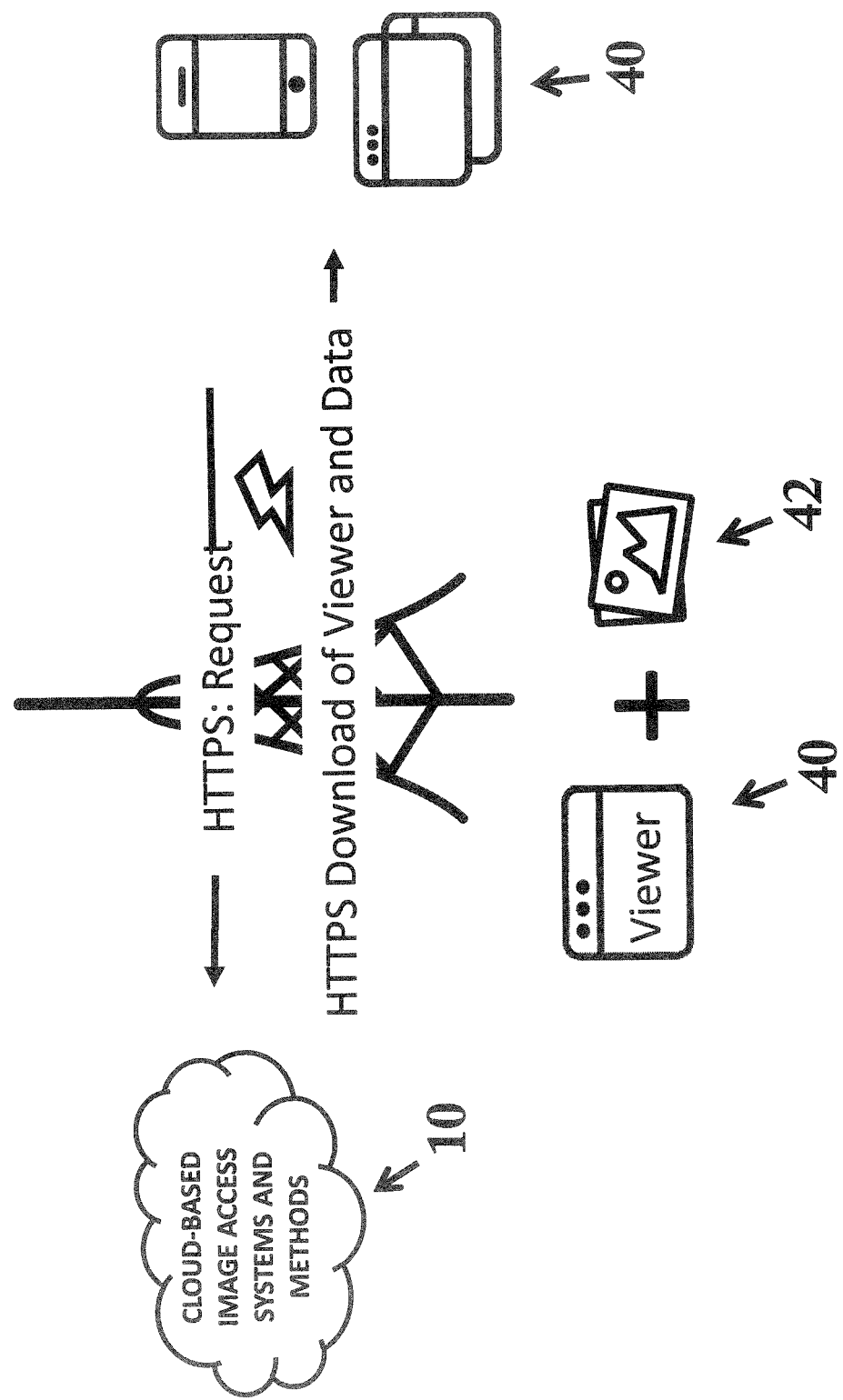

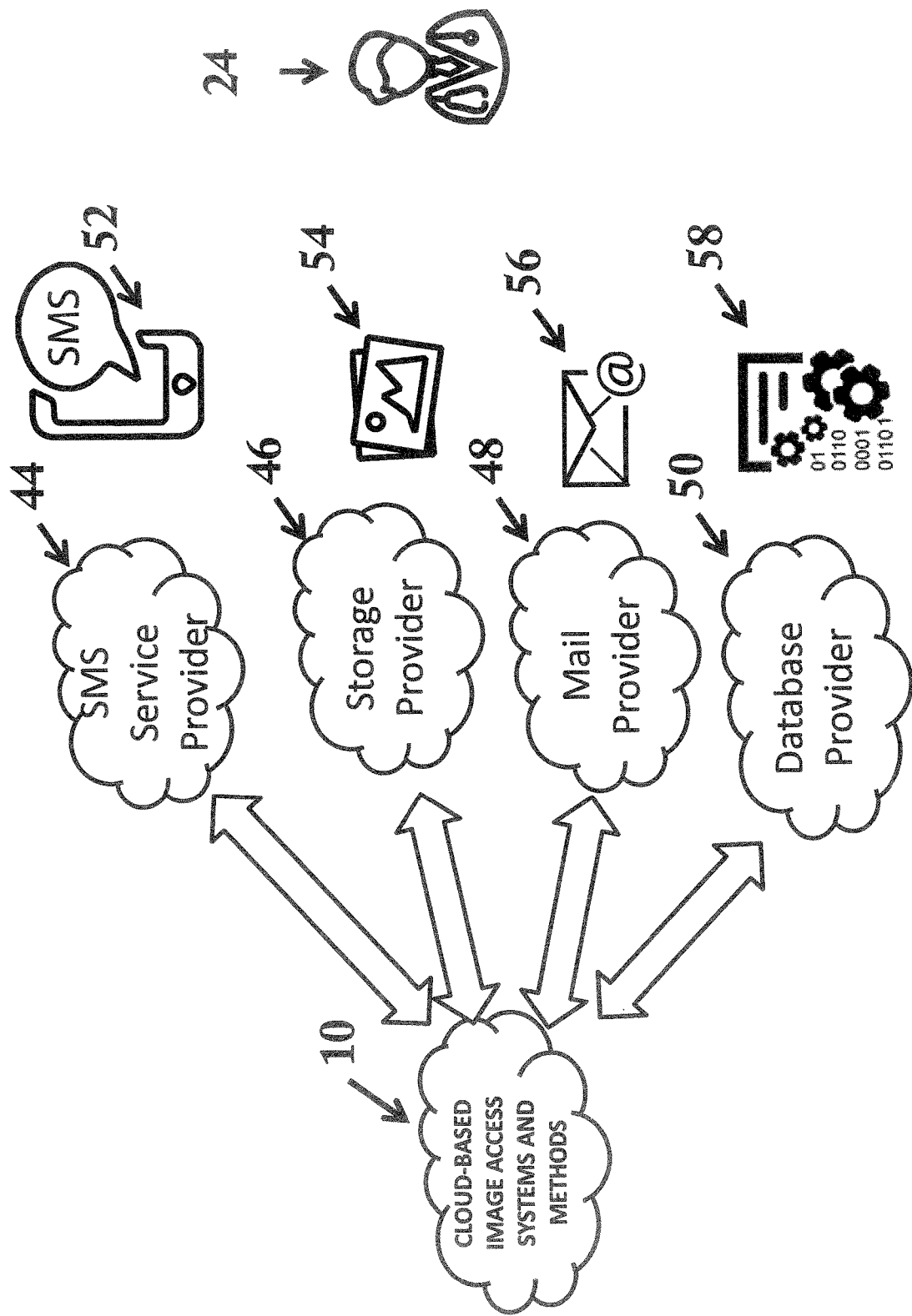

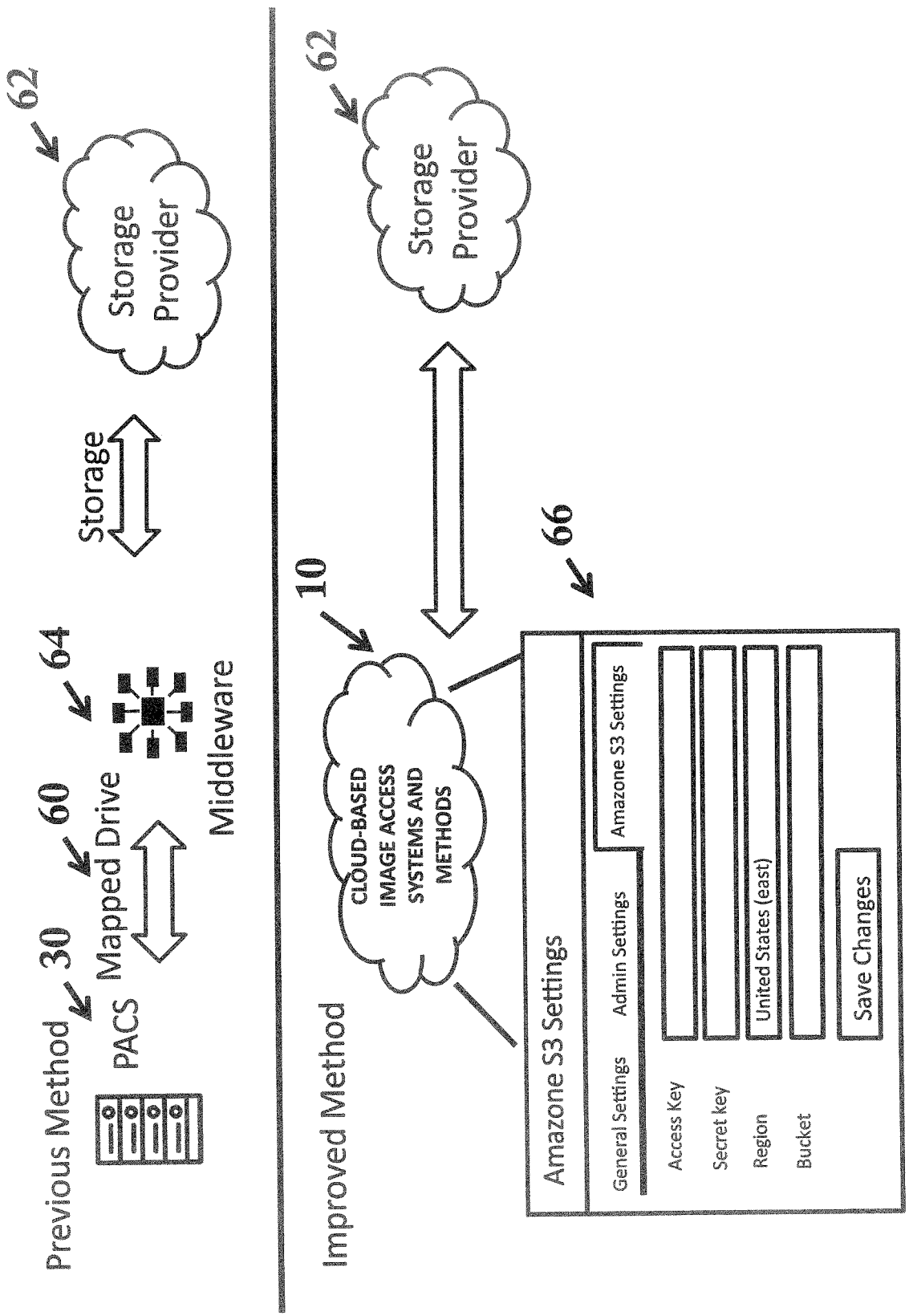

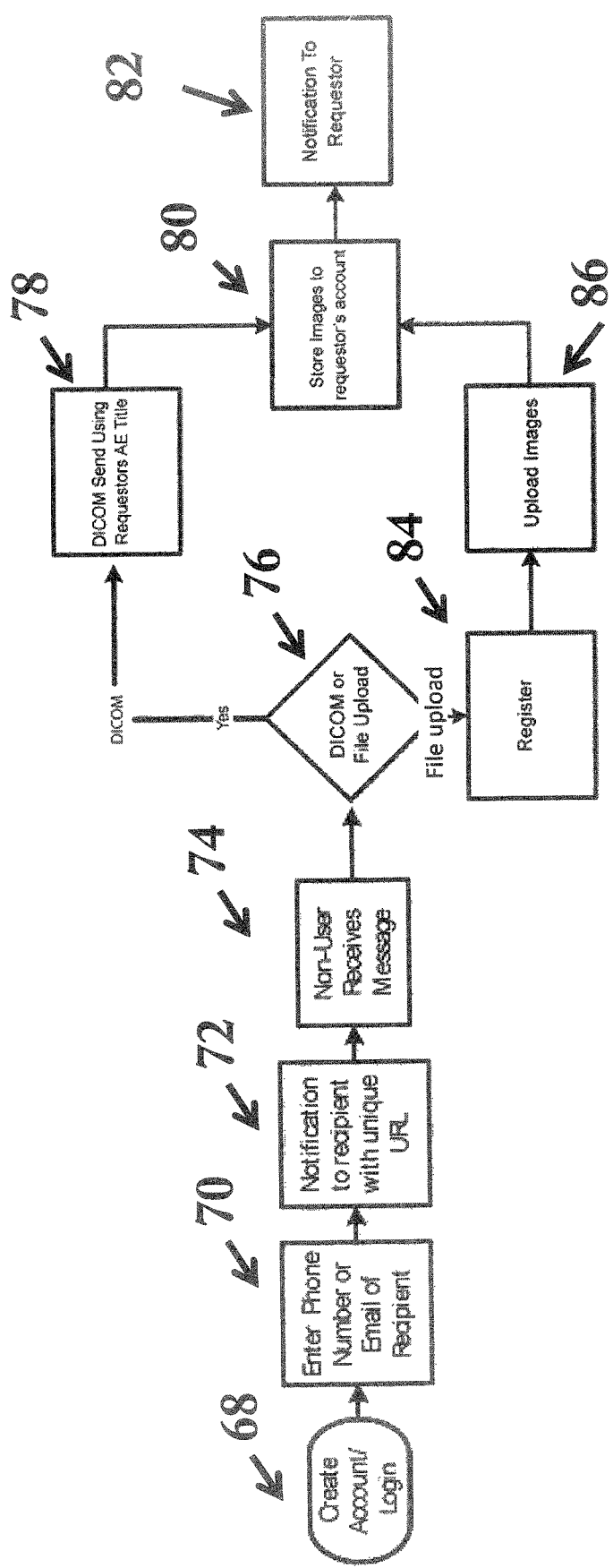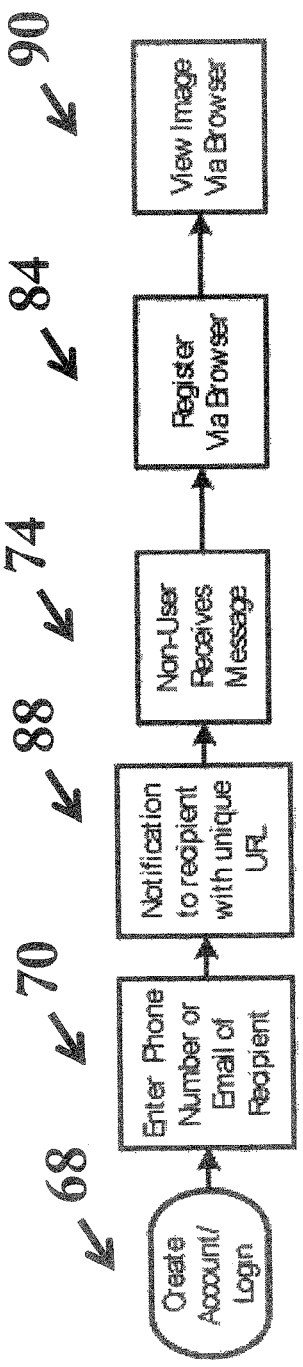
Figure 4A
Figure 4B

Traditional PACS Incoming communication flowchart

Improved Incoming DICOM flowchart

Figure 12

LOGO | Troy

New | Archive | Sent

EMAIL

Search

8 Items Found

| EMAIL | Patient Name | Status | Send At | |
|---|---|---|---|---|
| troy@trudef.com | Charles Faiya | Unread | 2017-04-18 | 4:00 PM |
| troy@gmail.com | | Read | 2017-04-18 | 2:00 PM |
| troy@trudef.com | Charles Faiya | Read | 2017-04-18 | 9:00 PM |

| Action | Patient Id | Name | Date Added | Descriptions |
|---|---|---|---|---|
| VIEW | 0 | Anonymized | April 1st 2020 | CXR |
| VIEW | 1763 | Wade Fisher | April 1st 2020 | CARDIAC |
| | | Wade Fisher | April 1st 2020 | |
| | | Dom Fisher | April 1st 2020 | Knee |
| | | Jen Fisher | April 1st 2020 | Finger |

Delete
DICOM Patient Informations
Invite
Invitations Sent
Sent To Archive
Download Study

RECEIVING CONTENT PRIOR TO REGISTRATION OF A SENDER

CROSS-REFERENCE TO RELATED APPLICATIONS

This application is a continuation of, claims priority to and the benefit of, U.S. Ser. No. 16/115,295 filed on Aug. 28, 2018 and entitled "CLOUD-BASED IMAGE ACCESS SYSTEMS AND METHODS," The '295 application claims priority to, and the benefit of, U.S. Provisional Ser. No. 62/552,373 filed on Aug. 30, 2017 and entitled "Improved PACS Systems and Methods." The entire contents of both are hereby incorporated by reference for all purposes.

FIELD

The present disclosure generally relates to sending, receiving, and storing medical images, and more particularly, to a cloud-based image access system and related methods.

BACKGROUND

Medical images generated from a medical grade acquisition device are not formatted or transferred like digital pictures from a camera. They are stored and transferred in a file format called Digital Imaging and Communication in Medicine (DICOM). Because all medical images closely resemble each other, DICOM files provide extra security measures so that patient images do not get confused. The acquisition device, such as an X-ray or magnetic resonance imaging (MRI) machines, writes the patient and image data inside the DICOM file. The information is stored on the DICOM header located at the beginning of the file. Only specialized software, which includes a DICOM viewer and picture archiving and communication system (PACS), can be used to transfer, view and store these images. The DICOM viewer and PACS are fashioned in a client/server relationship. The DICOM viewer is used by physicians to visualize and make diagnostic decisions and measurements. PACS are used to store and transfer DICOM files from a server. The DICOM viewer cannot store the images and the PACS do not have viewer capabilities. PACS are able to interpret the DICOM file headers and pass most of the DICOM information (from the header) to a database for later retrieval. They then store the DICOM image to a local disk or Network Attached Storage (NAS). The prior art techniques and systems for sending, receiving and storing medical images are flawed for a multitude of reasons, which will be explained below.

Sending Images Between Two Devices or PACS:

In order to send a DICOM image to another device, the sending device must have at least 3 identifiers regarding the destination in order to be received by that device or PACS. Much like phone numbers that are separated by country, area code and identifiers, the fields used in DICOM send are: the IP Address (e.g., 192.168.1.12), Port (e.g., 104), and AE Title (e.g., ACMEPACS).

The IP address is used to identify the device on a network. No two devices on a network have the same IP address. The port identifies the software instance on the device. No two applications listen on the same port. The Application Entity Title (AE Title) identifies a subgrouping of the device's software, which is specific to the PACS on the machine. No two PACS can have the same AE Title and exist on the same machine and IP. Each of the identifiers described above are specific to the machine, software, and PACS instance. The DICOM send process is designed to transfer images between two facilities or PACS securely. It can take hours, or in some cases days, to get new PACS and devices to communicate with each other. It often requires someone with knowledge of DICOM to manage the transactions at one or both ends. The system is, for the most part, a closed communication system and requires outside communication by the Administrators of each system. The three identifiers along with security protocols are usually unique to each machine, office, server, and location, requiring communication to occur outside of the system. The current system also lacks the ability to send images to individuals, patients, users, or a machine that is unattended.

Viewing of the Images:

Typical PACS operate in a client/server configuration in which the DICOM viewer must be installed on a user's work station before images can be rendered. This is very time consuming for deployment on a mass scale. An administration tool is required to grant users access to the database and file permission, which then will allow the application to query the database for a list of images and relevant data for that user.

Extensibility and Modality Responsive:

Because traditional PACS/DICOM viewers need to be installed and upgraded manually, they lack the ability to quickly respond to department or user needs. Often a machine that is deployed (say cardiology) will not be compatible with another department (say orthopedics) because different features are required.

User Management and New Users of the System:

Traditional PACS have multiple layers of security that require permission editing. The network environment, the database, and file system permissions need to be correct before a user is able to effectively view images. These often reside in separate management systems creating a burden on the users, administrators, and management of care providers. There currently is not a way to get new users into the system automatically. They must be manually input into each system.

Additional Data:

Traditional PACS and DICOM viewers lack the ability to introduce external data, such as pictures or PDF's, to a study or image set. Data in the PACS and viewer is typically limited to DICOM files and TEXT. For example, if a cell phone image needs to be stored with a study, it requires external communication (e.g. email). This separates some of the data from the DICOM files and database, and requires separate applications (e.g. PACS and Email) for the user to be able to see all pertinent data.

Notifications:

Users are typically not notified by the viewing application when images come in from an outside source. Constant monitoring of the work list (list of studies) of the PACS is required by user to see that new images are in. PACS and viewers lack the capability to interface with an Simple Mail Transfer Protocol (SMTP) server or SMS (text) gateway.

User Delegation of Images:

Often a single AE Title may be used for an entire department or group of users. The AE Title is not specific to a user. Lacking within a traditional PACS is the ability to assign an image or study to another user under the same AE title. To do so requires a specific rule be created by the PACS administrator to delegate conditions. For example: all MRI images go to User A, and all Ultrasound images go to User B.

Fixed AE Titles:

AE Titles are dictated by the PACS administrators usually at the time of set up, and are not easily changed. The DICOM sender MUST have the correct AE Title in order to successfully send images. If there is a miscommunication of the AE Title, when sending images between two devices/facilities, the images will be lost. No resiliency exists, which leads a very fragile transfer process.

Support of Cloud Services:

While cloud services continue to advance, tradition PACS lack the ability to interface with these services directly. They often depend on the service masquerading as a local service to the machine or network. They do not have the ability to adapt to services like Amazon S3 storage which uses a credential API to control. A $3^{rd}$ party application must be used to map a network drives and local resources to the cloud provider.

Device Agnostic:

Due to the nature of the client-side viewer, the current workflow and architecture of PACS require multiple client-side applications based on the OS (such as IOS and Windows) and department needs. If each version of the client-side viewer is not maintained, it can introduce security vulnerabilities and bugs. It is a constant challenge for the PACS administrator to maintain the native viewers on each machine, as well as the version specific to the OS.

DICOM Compliance at Browser:

Web based DICOM viewers exist but often require pre-processing of the DICOM image to a web compatible format such as Moving Picture Experts Group (MPEG), Joint Photographic Experts Group (JPEG), or Audio Video Interleave (AVI). This means users are viewing images that are not the source DICOM file, and therefore lack the DICOM header information. Potential security issues exist due to the similarity of patient images.

Issuing CDs to Patients:

It is a standard practice for imaging centers to issue a CD of the images taken to their patient for interpretation by a preferred physician. Given this practice it is the patient's job to deliver the CDs to an interpreting physician for review. These CDs degrade over time and can easily be misplaced or confused with older images.

Second Opinions by the Patient:

At times, a patient may want to request a second opinion. The availability of such field experts is typically inconvenient. With the inability of most patients to transfer image files over a cloud service, the CD of the DICOM files is mailed to the physician. Time is usually of the essence for studies such as this, and yet the patient is lacking a useful tool to help them seek out the best medical advice in a timely manner.

Physician to Physician Consults:

Medical professionals often consult with their peers about certain studies or cases to provide the best patient outcomes. This process introduces an additional burden if DICOM images are involved. Setting up a DICOM send for a single study, if for example a physician works at Hospital A and his peer works for Hospital B, is time consuming. Hospital B is not required to use company resources for such transactions and image storage. This often means the consulting physician needs to use his own resources to view the images. Pictures taken by a cell phone of the DICOM viewer are frequently used between consulting physicians. This has an obvious negative effect of the quality of the image.

Receiving Images from a Patient:

Image acquisition often happens outside the facility of the treating/interpreting physician. The patient is given a CD of their imagines by the imaging center. An appointment is then set up to review the images with the patient in order to explain a treatment plan or diagnosis. The imagines on the CD are typically not shared with the physician until the time of the appointment, leaving the physician in charge of opening the DICOM files while the patient is in the exam room. This consumes valuable time for both parties and the facility, and is rarely successful.

SUMMARY

The system may include a method comprising requesting, by a computer, a receiver identifier associated with a receiver; receiving, by the computer, the receiver identifier in association with content; constructing, by the computer, a URL link comprising access to DICOM viewer code, DICOM data for the selected images, a sender identifier and the receiver identifier; generating, by the computer, a notification to the receiver, wherein the notification includes the URL link; and transmitting, by the computer, the notification to a receiver based on the receiver identifier.

The content may be a medical image and the medical image may only viewable with DICOM viewer code. The notification may further include at least one of a sender name or a description of the content. A sender name may obtained from a sender profile. The receiver identifier may be at least one of a receiver email address, receiver cell phone number or a receiver social security number. The method may combine notification functions, DICOM functions, and/or browser-based encryption functions. The notification may comprise viewer application code, content to be viewed, an identity of the sender and an intended receiver. The method may send the notification through secure HTTPS. The method may send the notification via transfer of non-compiled java and html code. The method may not require prior communications between the sender and recipient to overcome firewall and security settings.

The URL link may further comprise a description of the content obtained from the DICOM header. The URL link may further comprise a description of the content obtained from a description field and the description field may be populated by the sender.

The method may receive a request images instruction. The method may receive the receiver identifier from an image access system that is capable of transferring files over DICOM protocol, in response to the sender not being registered. The method may receive an IP address and port number, in response to the sender not being registered. Moreover, the images may be held until the recipient registers.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIG. 1 is an exemplary diagram illustrating an overview of an image access system with unified communication of DICOM images, notifications, and secure file transfer according to various embodiments.

FIG. 2B is an exemplary diagram illustrating the image access system in use with a mobile device (e.g. mobile phone) to deliver the viewer and patient data together specifically for mobile devices with an internet browser.

FIG. 3A is an exemplary diagram illustrating how the image access system interfaces with any of a variety of on-demand cloud service providers, including but not limited to SMS (text), data storage, email, and database providers.

FIG. 3B is an exemplary diagram illustrating for comparison the prior art method of indirectly interfacing with cloud service providers via middleware (top half of FIG. 3B) and the improved method of directly interfacing with cloud service providers via the image access system according to various embodiments (bottom half of FIG. 3B).

FIG. 4A is an exemplary flow chart illustrating how users of the image access system may request images from a non-registered user according to various embodiments.

FIG. 4B is an exemplary flow chart illustrating how users use the image access system to send DICOM images to a non-registered user according to various embodiments.

FIG. 12 is a representation of an exemplary solution, illustrating the feature to send multiple images to multiple emails according to various embodiments.

Figure 14:
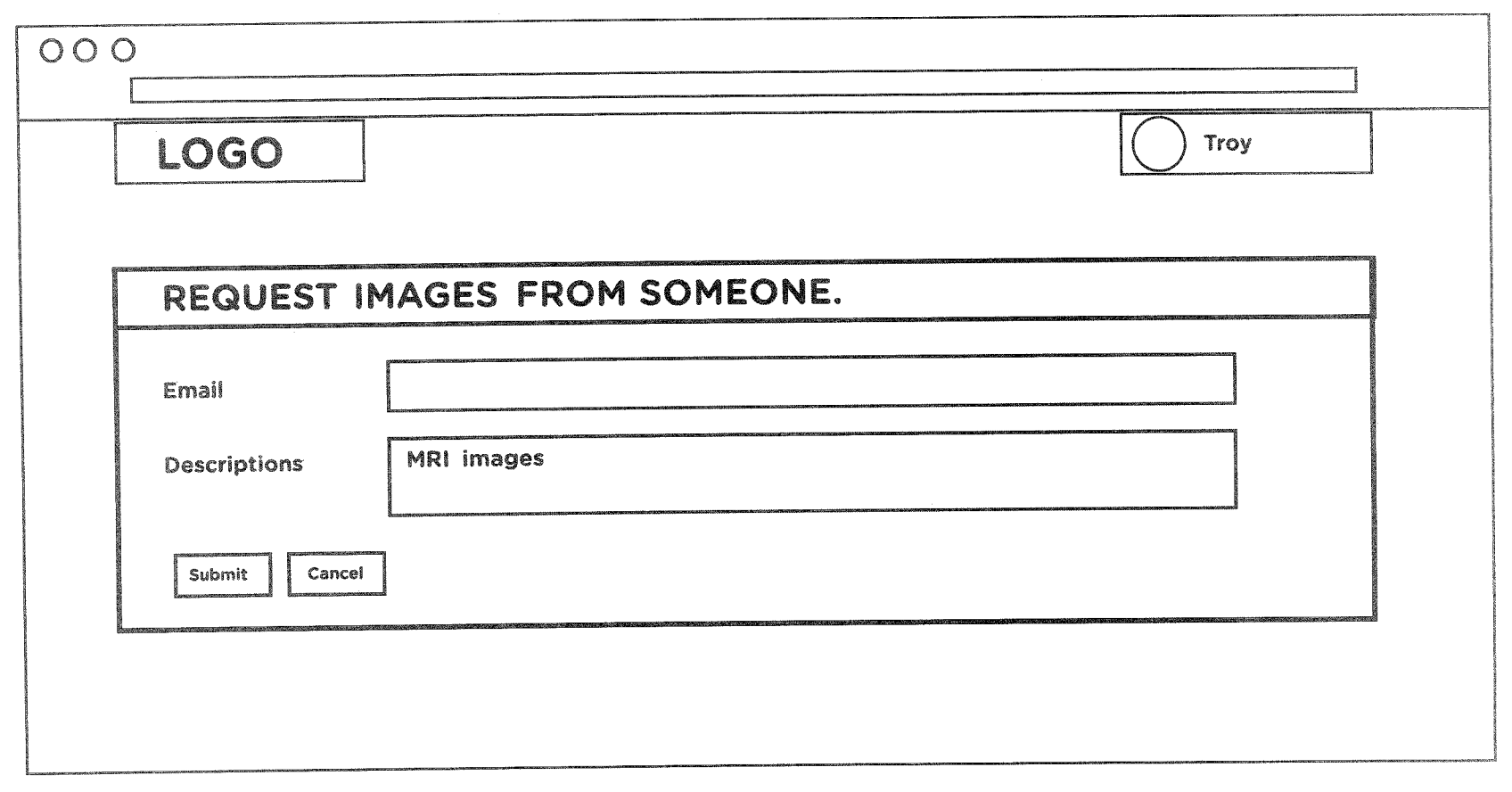

FIG. 14 is a representation of an exemplary solution, illustrating the feature to send a study to an email according to various embodiments.

FIG. 20 is a representation of an exemplary solution, illustrating the menu and work list of studies according to various embodiments.

DETAILED DESCRIPTION

Figure 2A:
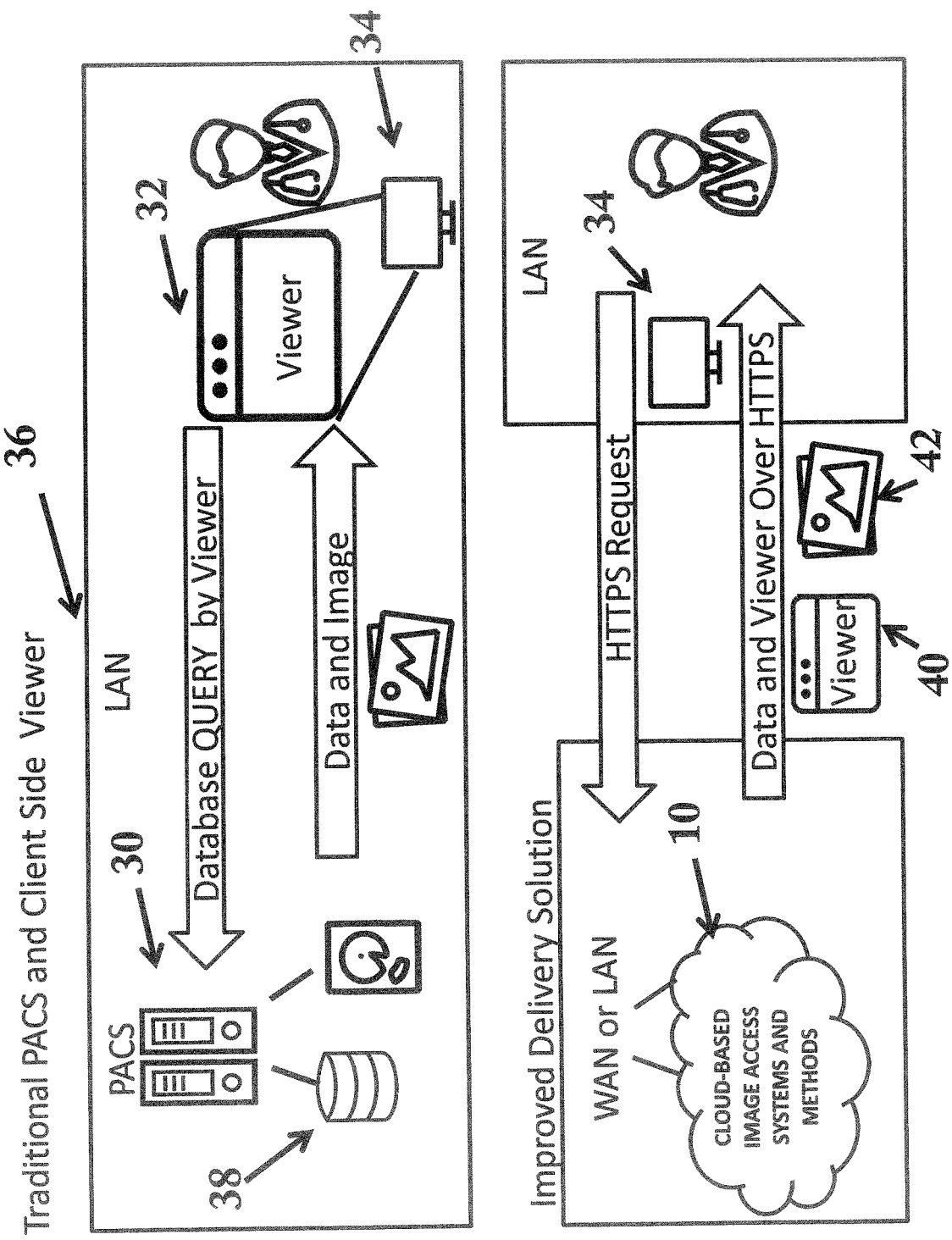
FIG. 2A is an exemplary diagram illustrating for comparison the request and delivery of data and images using a traditional PACS and client-side viewer (top half of FIG. 2A) and using an image access system according to various embodiments (bottom half of FIG. 2A).

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages. In the interest of clarity, certain known features of an actual implementation may not be described in this disclosure. The system may include compliance with system-related and business-related constraints, which will vary from one implementation to another.

The image access system and related methods of the present disclosure may take any of a variety of suitable forms, including (for example) proprietary computer software program(s) capable of operating on and communicating between any of a variety of suitable computer systems, databases, telecommunication systems, and the like as described herein and/or readily ascertainable by those skilled in the art based on currently available or later developed technology. The software program forming part of the image access system allows any number of stakeholders (e.g. patients, healthcare professionals, care-givers, family members, etc.) to enjoy and leverage a host of features and functionality which are improvements over the prior PACS system and techniques. The improvements include, for example: 1. Storing and viewing raw scan data for medical diagnostic imaging that contains enhanced architecture conducive to improved communication methods and onboarding of non-registered users. 2. Delivery of viewing technology, patient data, and patient image data over internet connections utilizing a web browser application on any device, which enables rendering of the DICOM file directly on the web browser. 3. An extensible architecture for image access that allows 3rd party cloud services to handle much of the workload independent from the platform. 4. Direct communication between an image access system and 3rd party cloud service providers instead of through middleware or security translation. 5. Enabling an image access system to have dynamic Application Entity Titles (AE Title) in order to route images to a specific users or login. 6. Enabling an image access system to process user data for use in the incoming AE Title for receiving medical images. 7. Enabling an image access system to accept any image regardless of AE Title and route the data to a user based on AE Title alone. 8. Enabling an image access system to accept any image regardless of AE Title and hold the data until a user matching the AE Title has registered in the system. 9. Analyzing the incoming AE Title for communication data such as phone number or emails. 10. Requesting that medical DICOM images be sent to non-registered users. 11. Transferring (sending) medical DICOM images to non-registered users. 12. Delivering a customized user interface based on user type of an image access system user. 13. Indexing non-DICOM electronic material to a patient's study or image over a browser. 14. An extensible image access system architecture conducive to cloud service providers, user login types, browser side DICOM rendering, and external communication types such as email and SMS text. 15. Ability to send/request images, via DICOM protocol, to non-registered users based on the sender knowing a data point about the non-registered user (such as email or phone), which will eliminate the need for burning CD's and automates the data needed for device to image access system communication.

FIG. 1 is an overview of an image access system 10 with unified communication of DICOM images, notifications, and secure file transfer among a multitude of entities within the healthcare continuum, including systems, facilities, and users. Systems may include, for example, acquisition device(s) 12 (e.g. MM, CT, and X-Ray systems) for generating digital images of a patient and image access system(s) 14 for maintaining image archives and communicating images to other locations. Facilities may include, for example, a primary healthcare facility 16 (e.g. office, clinic, or hospital where a patient goes to obtain primary healthcare services, such as primary physician visit) and a secondary healthcare facility 18 (e.g. office, clinic, or hospital other than primary healthcare facility where the patient goes for secondary care, such as second opinion, surgery, etc.). The primary healthcare facility 16 and secondary healthcare facility 18 may be part of the same healthcare system (e.g. hospital chain, etc.) or part of separate and distinct healthcare systems. Users may include, for example, unregistered users 20, patients 22, and healthcare providers 24. Unregistered users 20 may include, for example, individuals, businesses, or groups who have not created a login to access and use the image access system. Healthcare providers 24 may include, for example, general practitioner physicians, surgeons, physician's assistants, scheduling coordinators, nurses, etc.

The image access system of the present disclosure enables robust and convenient communication amongst the various entities through functionality including, for example, notifications (e.g. SMS text, email), secure file upload/download, and DICOM send/receive as shown in the boxed legend of FIG. 1. In various embodiments, the image access system may employ known in the art secure file upload/download and known in the art DICOM send/receive functionalities between and amongst all the entities in the continuum, while the notification functionality may be employed for all except the acquisition device(s) 12 and image access system(s) 14. The various communications and functionalities within the image access system 10 may be provided with any of a variety of currently available or later-developed encryption techniques or tactics to help prevent unauthorized access to the system and any data (in motion and/or at rest) and communications associated therewith.

The image access system allows any entity to send/receive DICOM files automatically with limited input from users or image access system administrators. This has been impossible in prior art image access systems because the prior art systems are only designed to send between two PACS software programs (PACS to PACS, see, e.g. FIG. 5C). Patients simply do not own PACS software so giving them the ability to send or receive their images was previously impossible. The image access system eliminates or reduces the need to burn and mail DICOM images on a CD to patients, doctors, or care providers. By combining notifications, DICOM functionality and browser-based encryption, each entity can send to any other entity (e.g., in the diagram of FIG. 1). More particularly, the functions of notification, DICOM functions, and browser-based encryption are combined by sending the viewer application code, the data to be viewed, and the identity of the sender and intended receiver through secure HTTPS transfer of non-compiled java and html code. The solution also accommodates unregistered users by invitation over a notification system. As such, the DICOM software and/or viewer does not need to be installed on the client system. The DICOM software and/or viewer may be embedded in a webpage and opened in a browser by the client system.

The largest obstacle in sending images to another location via traditional PACS is the constant need of prior communications between server administrators, on each end, to navigate firewall settings and security before a send can be completed successfully. The image access system of the present disclosure overcomes this limitation by using personal identifiers (frequently known by the sender, such as email or phone number—per FIG. 5A) such that the sender and the receiver do not have to communicate outside of the image access system prior to images being sent. All data traffic is conducted on a commonly open firewall for web browsing and email. The following examples illustrate common situations where the image access system overcomes the limitation of the need for prior knowledge of static communication values.

Example 1. If a registered physician would like to send DICOM images to another physician who is unregistered, the sending physician simply presses send next to the images to be sent and enters the receiver's email address that is requested by the system. Once the physician enters the receiver's email address and selects ok, the image access system constructs a unique and secure url link that is capable of providing access to and/or delivering DICOM viewer code, DICOM data for the selected images, and identity information for the sender and intended receiver. The solution then generates an email to the recipient (receiver) stating the senders name, a description of the images, and a unique url link for accessing and viewing the images. The system manages the permissions for receiving the notification and accessing the link. The system determines who to send the message to. The sender name may be obtained from a sender profile associated with a sender account. In various embodiments, the user account may need to be logged in, in order to obtain the sender name. In various embodiments, the description of the images is obtained from the DICOM header, if a description is included. In various, embodiments, a description field is offered to the sender, for example, along with the field allowing entry of the receiver's email address.

Example 2. If a registered physician would like to send DICOM images to another physician who is unregistered, the sending physician enters the receiver's cell phone number and a SMS Text message will be sent to the receiver with the similar information contained from Example 1.

Example 3. The reverse problem exists when a physician would like to receive and view images, but lacks the ability to contact the potential sender. This happens frequently in the medical specialty of orthopedics, where a patient oftentimes needs to schedule an appointment for the sole purpose of delivering a CD containing their images so the orthopedic surgeon can review them for diagnostic or second-opinion purposes. The physician is then tasked with loading the images into a viewer while the patient is waiting. The image access system allows the physician to request images from the patient prior to the appointment.

The physician simply selects "request images" from a drop-down menu within the software of the image access system and enters the patient's email address. The image access system generates a request for images email giving the user instructions how to send the requested images from any computer (a CD drive may also be used to upload the images). The image access accomplishes this by including in the image request email a unique url link that associates DICOM images sent following that link to the requester's account. The image request email also contains unique DICOM communication settings for the requester's account should the recipient of the request chose to send the images using DICOM protocol.

Example 4. In various embodiments, the above examples have one user (sender or receiver) registered, but the image access system goes a step further in allowing both parties to be unregistered users at the time images are sent over DICOM protocol, as illustrated in FIG. 5D. For users to send images without registering, in various embodiments, the sender uses an image access system that is capable of transferring files over DICOM protocol.

The sender simply types in the IP and Port number of the solution, and then enters a personal identifier of the recipient (such as a cell phone number). The images are accepted and held in the image access with a status that indicates that the recipient and/or sender does not have a registered account associated with the recipient until the recipient and/or sender registers with a matching identifier (e.g. cell phone, email, etc. . . . ). Upon new account registration, the purgatory list of images is checked for matching credentials. In various embodiments, the act of registration causes the image access to look for matching credentials. In various embodiments the image access uses a timer to check periodically. If matched, the status of the purgatory images are set to claimed and viewable by the account holder. In various embodiments, the image access uses verified email addresses and mobile numbers to qualify matching credentials or any established set of verifiable criteria can be used. The image access system goes yet another step further to deliver hands free administration. The image access system includes functionality capable of recognizing the personal identifier being input by a user and sending a notification to the user informing them of the existence of images previously loaded into the image access system, potentially prior to their registration. In various embodiments, the act of a personal identifier being input would trigger the image access to look for existing images associated with that identifier. In various embodiments, the image access may use a timer to perform this check at intervals. This is depicted in FIG. 5D. This is especially useful for imaging centers, which only do image acquisition and thus are limited to transporting images via image access system to other locations or providing the patient with a CD. With the advent of the image access system of the present disclosure, imaging centers will have the ability to send all images to the image access system using an email address or cell phone number as opposed to using the AE Title (employed in the prior art PACS systems). The image access system does the remainder of the work, allowing the recipient to electronically receive, view, save, or forward on the images for additional review.

FIG. 2A illustrates for comparison the request and delivery of data and images using a traditional PACS and client-side viewer (top half of FIG. 2A) and using the image access system 10 of the present disclosure (bottom half of FIG. 2A). The traditional PACS system includes a hardware-based PACS on a server 30 communicatively coupled to a hardware-based drive 31 and PACS database 33, as well as a client-side viewer 32 installed on a computer 34 that is on the same local area network (LAN) 36. Upon initiation by a user (e.g. computer keystroke, mouse click, etc.) the viewer 32 sends a query to the PACS database 38 for requested patient records and images. The requested patient records and images are then transmitted back to the viewer 32 and then displayed to the user on the computer 34.

As shown on the bottom half of FIG. 2A, the image access system 10 provides a more flexible work environment for viewing images securely across a local area network (LAN) and/or a wide area network (WAN) by delivering the viewer, data, and images together. The image access's viewer requires no installation and is sent to the browser preconfigured. An interface is presented to the user and DICOM data is streamed, from storage, to the viewer. This process is in contrast to prior art systems that require installation and configuration prior to use.

The image access system 10 may be run on either a cloud-based service and/or installed on hardware-based networks (LAN or WAN) within a hospital. Upon initiation by a user (e.g. computer keystroke, mouse click, etc. . . . on the computer 34), a HTTPS request is sent via the browser on the computer 34 such that it can bypass any firewall, via a public port, employed as part of the LAN or WAN. The viewer 40 used with the image access system 10 and the requested patient data 42 (e.g. records or images located on the LAN or WAN are rendered in the image access system 10 then delivered together to the user device over HTTPS. In this manner, the image access system 10 is very resilient and can deliver the viewing technology, along with the images, to any browser accessible around the world. This is especially important in the medical field where patients are often in remote areas far from specialty physicians who are spread throughout the world.

FIG. 2B illustrates the image access system 10 in use with a mobile device 40 (e.g. smart phone, tablet computer, laptop, etc.) to deliver the viewer and patient data together specifically for mobile devices with an internet browser. Upon activation by the user of the mobile device 40, an HTTPS request will be transmitted wirelessly (e.g. via cell tower, WIFI, satellite, etc. . . . ) to the image access system 10 which will render the requested patient data 42 and then deliver along with the viewer 40 to the mobile device 40 user device over HTTPS. By delivering the viewer, images, and patient data together, the image access system 10 allows any device with an internet browser to access patient images without a preinstalled client application. The viewer and data can be downloaded over cell phone or satellite data communication link. Using advanced programming methods in Java Script, the solution converts the pixel data and DICOM information to raw pixel data and readable text in the browser. The system stores the pixel data temporarily in the browser's memory and renders it on the screen (e.g., in java script), thereby tricking the browser into believing it is a native image. This is important because it is "read only" access and does not alter the DICOM file(s). Altering the DICOM files on the server, for example, would create a central point of failure and does not follow the "Chain of Custody" demands of many health care providers. If a server-side application where to convert the DICOM data, then two copies of the same images would exist—one in DICOM (the original) and one for web compatibility (for viewing over the web).

FIG. 3A illustrates how the image access system 10 integrates directly with cloud-based service providers to allow extensibility, scaling, and more efficient delivery of services such as messaging. The image access system 10 may be installed on any of a variety of computers systems, including (for example) desktop computers, laptop computers, network computers, virtual computers, mobile devices, etc. . . . The image access system 10 may be used with any of a variety of currently available or later-developed cloud-based services, including (for example) Amazon, Google, etc. The type of cloud-based services may include, for example, SMS/text 44, data storage 46, email 48, and database 50 capable of generating the respective service output, namely, SMS/texts 52, data 54, email 56, databases 58. The extensibility enabled by cloud-based services allows the image access system 10 to overcome issues with local and regional internet service providers (ISPs). For example, many ISPs block or forbid sending mass email volumes in an effort to prevent SPAM. The image access system 10 does not need to adhere to the terms of service because it can use a third-party provider to send outgoing mail. In other words, in various embodiments, the system bypasses local or regional ISPs because the server software is cloud based and can utilize any email provider directly. By communicating over application programming interface (API), the image access system 10 is able to send the data to the cloud-based service provider for the provider to send the data out. Traditional PACS systems are not extensible because they operate on a firewalled LAN. In contrast, the system may rely on third parties to provide hard drive storage, notifications, SMS, and authentication. An example of email data may look like this:

```
API User: switchpacs
API Key: 1234ABCD5678910
{
    "data": [{
        "type": "email",
        "id": "1",
        "attributes": {
            "title": "You have received medical images from $sender!",
            "body": "$User has sent you medical images. To view them click here .",
            "created": "2016-05-22T14:56:29.000Z",
            "updated": "2016-05-22T14:56:28.000Z"
        }
    }
    }],
```

Through the use of the image access system 10, this script may be passed to the third-party via the internet (http:// or https://) such that the third-party can process and parse the data as it relates to delivery to a user. The third-party can then route and deliver the messages to the appropriate individual as an outgoing email. The data is then generated by the third-party as email and sent out, as opposed to using the ISP that the image access system 10 is hosted on.

FIG. 3B illustrates for comparison the prior art method of indirectly interfacing with cloud service providers via middleware (top half of FIG. 3B) and the improved method of directly interfacing with cloud service providers via the image access system 10 (bottom half of FIG. 3B). Traditional hardware-based PACS 30 include a mapped drive 60 which makes the cloud service 62 appear as a local disk to the server hardware. While they are able to integrate with cloud service providers 62, it requires translation software (e.g. middleware 64) to do translation or authentication conversion to adapt to the cloud service 62.

The image access system 10 has the settings built directly into the application that talks with the data and the authentication protocols directly without the need for middleware. More specifically, with reference to the bottom half of FIG. 3B, the image access system 10 can interface with the cloud storage provider service 62 (e.g. Amazon S3 by way of example only) and includes embedded security information 66 within the software of the image access system 10. The image access system 10 uses the data-storage resources of the cloud-based service 62 to send data to the user's browser. In so doing, the image access system 10 provides a virtually unlimited data storage capacity via the cloud-based service provider 62. The embedded security information may include, for example, every time a connection is made with a third party API, credentials are passed and verified. For a traditional PACS to extend storage to the cloud, it must "trick" it's host server into believing it has a large hard drive. This is commonly known as "Drive Mapping". Middleware must be used to pass the API credentials to the storage provider to store the data.

FIG. 4A is an exemplary flow chart illustrating the process of a registered user requesting images from a non-registered user. Users may include, for example, individuals or groups of users, already registered in the system. Non-registered users may include for example, any individual who is not currently registered in the system.

In the presented scenario, the process starts with the user registering (e.g. creating an account.) or logging in to the interface 68. The interface is, for example, a web page or user interface on a device (i.e. mobile phone, laptop, workstation, etc). The image access system then has an interface for the user to request images. In various embodiments, the software is delivered via a browser. The user is able to type an identifier (e.g. cell phone, email, etc) of the intended receiver into the interface 70. The receiver is, for example an individual, care provider, physician, or group of users that may or may not be registered in the system. A notification is generated and sent to the recipient 72. In various embodiments, this is done via a third-party email or SMS solution. In various embodiments, other email or SMS delivery methods may be used. The image access determines the method of communication (either email or SMS) by reviewing the supplied identifier and using logical routines. The notification contains, for example, the Requestors (e.g. asking user) AE Title(s) and/or a unique URL (link) for the recipient to upload images. In various embodiments, any data can be part of the AE Title such as, for example, text number, email address, etc. (in contrast to prior PACS systems that require the AE Titles to match exactly). The system can then automatically recognize the port and IP address. The recipient receives the notification 74. The recipient has the choice to upload or send images via DICOM protocol 76. If the recipient chooses to send via DICOM protocol, then they send the images, from their device or image access system, to the Requestors information sent through the notification 78. The recipient may choose based on their experience and allowed access. For example, an image access system administrator may choose to send via DICOM send because they have authority and it is easiest for the administrator. An office worker may not have the same access and then will likely choose the included link to the upload page. To upload the files over https://, the recipient may follow the unique URL link supplied in the notification requesting a registration to the system 84 (link included in the image request email). Once registered, they have the ability to upload the images 86 to the requestors' account 80. A notification may or may not be sent to the requestor 82. In various embodiments, the unique URL directs the user to an interface to upload images without requiring registration.

This process can be used in many circumstances, for example, such as:
Doctor (user) 24 requesting images from patient 22
Patient (user) 22 requesting images from a Care Provider 16
Hospital (user) 16 requesting images from another Care Provider 18

By using generated dynamic notifications 13, the image access system 10, automatically delivers instructions how to send images to the requestor. Instructions include, for example, in the form of written text and/or combination of media (such as pictures and movies, directions for an individual to follow for the purpose of completing a task. The instructions contain, for example, how to transfer via secure file upload 15, user specific DICOM information, and other transfer information. The email, or SMS text, consists of information about requestor and specifies what images they are looking for. For example if Hospital A 16, is registered in the solution, and needs images from Hospital B18: Hospital A 16 clicks on "Request Images" and enters Hospital B's 18 email. Hospital B 18 receives an email or text, similar to: (for example). (System variables are in [brackets]):
To: hospitalB@domain.com[recipient]
From: email@solution.com[solution]
Subject: Hospital A [requestor] has requested images from you
Body: Hospital A [requestor] has requested images from you regarding: Patient Jane Doe, CT that was taken on or around 1/1/2001[description of images]. To send these images upload to http://[solution]/[unique url]. Alternatively, Administrator may do a DICOM send Operation to:
IP: 123.123.123 [solution IP Address]
Port: 105 [solution Port number]
AE Title: HospitalA@domain.com[email AE Title of requestor]
OR
AE Title: 9876543210 [phone AE Title of requestor]
The above email is sent to the intended recipient with instructions to complete a send operation to HospitalA.

FIG. 4B illustrates the process of a user sending images to a non-registered user. The sender must login or create an account in the system 68. Once logged in they choose the images they would like to send, from the works list, and select "Send". The sender is prompted for the recipient's email or phone number 70 within an interface dialog. The notification is generated containing a unique URL (link) 80 A new link may be generated for each send, wherein the link is unique for that specific send of images, and the receiver gets the notification 74. The receiver then clicks on the URL to be taken to a special registration page. When registration is completed 84, the receiver is able to view the images 90. The url is a link that displays the viewer and populates it with appropriate data and images.

This process can be used in many circumstances for example:
When a patient (user) wants a second opinion from a doctor
When a doctor (user) want to consult with a colleague about patient images.
When a Doctor or Patient (user) wants a specialist to view images for diagnostic purposes.

For example if Hospital A 16, is registered in the Image access System, and wants to send images to Hospital B18: Hospital A 16 clicks on "Send Images" and enters Hospital B's email. Hospital B 18 receives an email similar for example: (solution variables are in [brackets]):
To: hospitalB@domain.com[recipient]
From: email@solution.com[solution]
Subject: Hospital A[sender] has images for you to review
Body: Hospital A[sender] has sent you images: To view these images go to http://[solution]/[unique registration url].
The above email is sent to the intended recipient. The link sends the user to a unique registration page. After filling out the registration, the user is redirected to viewing of the images.

Figure 5A:
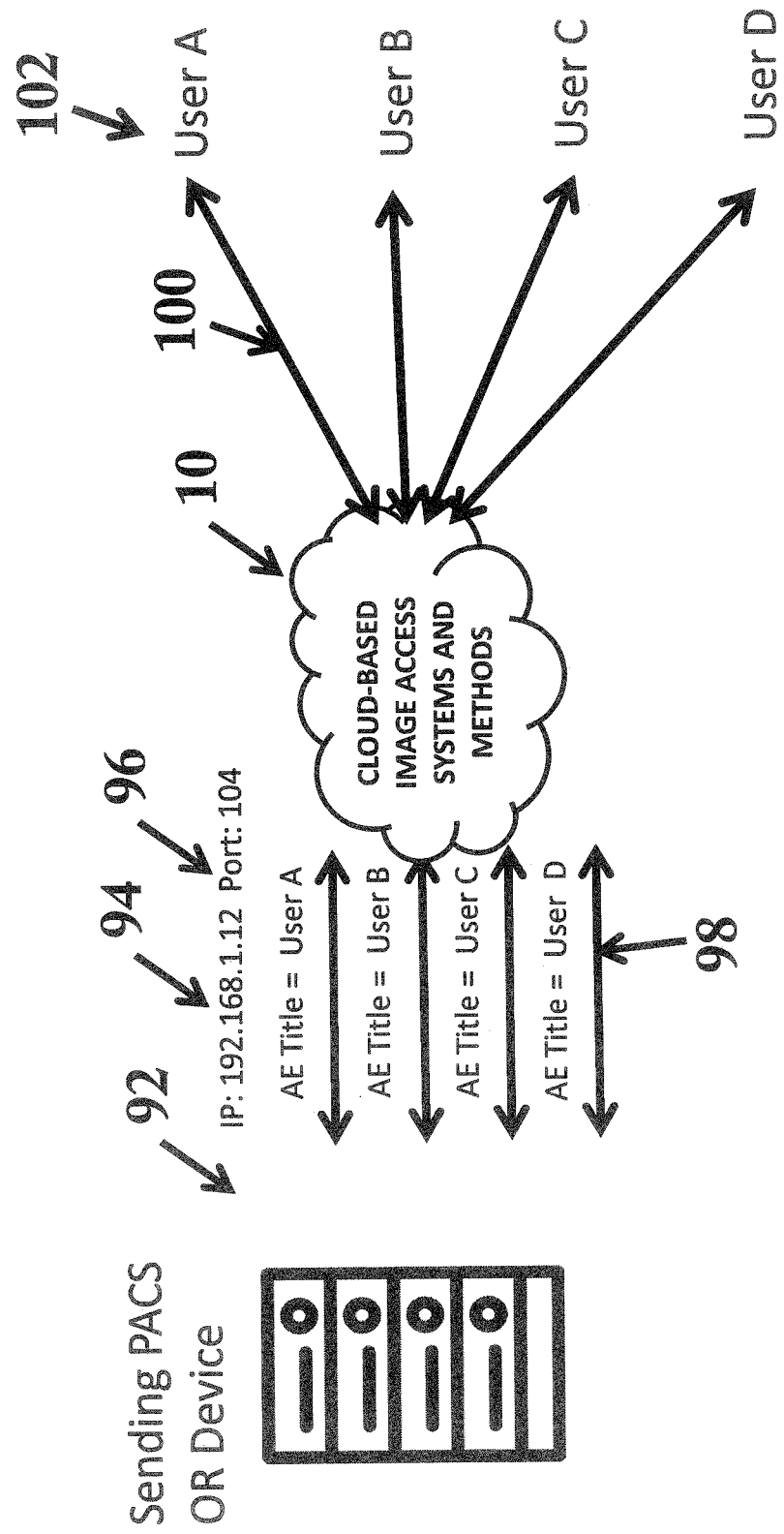
FIG. 5A is an exemplary diagram illustrating a data delivery method of the image access system using the AE Title to route images to the intended recipient according to various embodiments.

FIG. 5A illustrates a flow chart for a new and improved approach to receiving medical images over DICOM protocol from an image access system or Device. This includes for example a LAN or WAN connectivity. Instead of the receiving AE Title being preconfigured and static on the receiving side (FIG. 5C), the Image access System 10 is able to receive images directly 98, to a user's account 102, by analyzing the AE Title 98 The database may hold user data. The AE title may be used to associate the image to the account for user specific data. When sending images from an image access system or Device 92, the administrator is requested to enter 3 variables about the receiving image access system or Device: IP Address 94, Port 96, and AE Title 98. The Image access System queries the database for unique personal data points of a user's account, in order to route the data appropriately 100. In various embodiments, the query is completed in response to a new user signing up. In various embodiments, a timer controls this process at periodic intervals. This is vastly superior to previous PACS methods of having static AE Titles.

Each user on the solution has a number of personal identifiers such as cell phone, email, username. As long as the personal identifier is unique to the user it can be utilized. The personal identifier may be something less public like patient ID or Social Security Number. Having a less public identifier increases the security of the solution so that only the two parties (sending and receiving) know the identifier. For example if an imaging center would like to send images to a patient, using the Image access System, they might use the patients Social Security Number. As long as the receiving user fills in the Social Security Number correctly, they will receive the images to the corresponding account. A flow chart demonstrating this is FIG. 5D. In this example, your SSN, nickname, and a personal code may be stored in a profile with your email provider. When someone sends an email to your provider, but doesn't use your email address, they instead use your SSN. The email provider may route the message to your account because they matched the SSN to your profile.

Figure 5B:
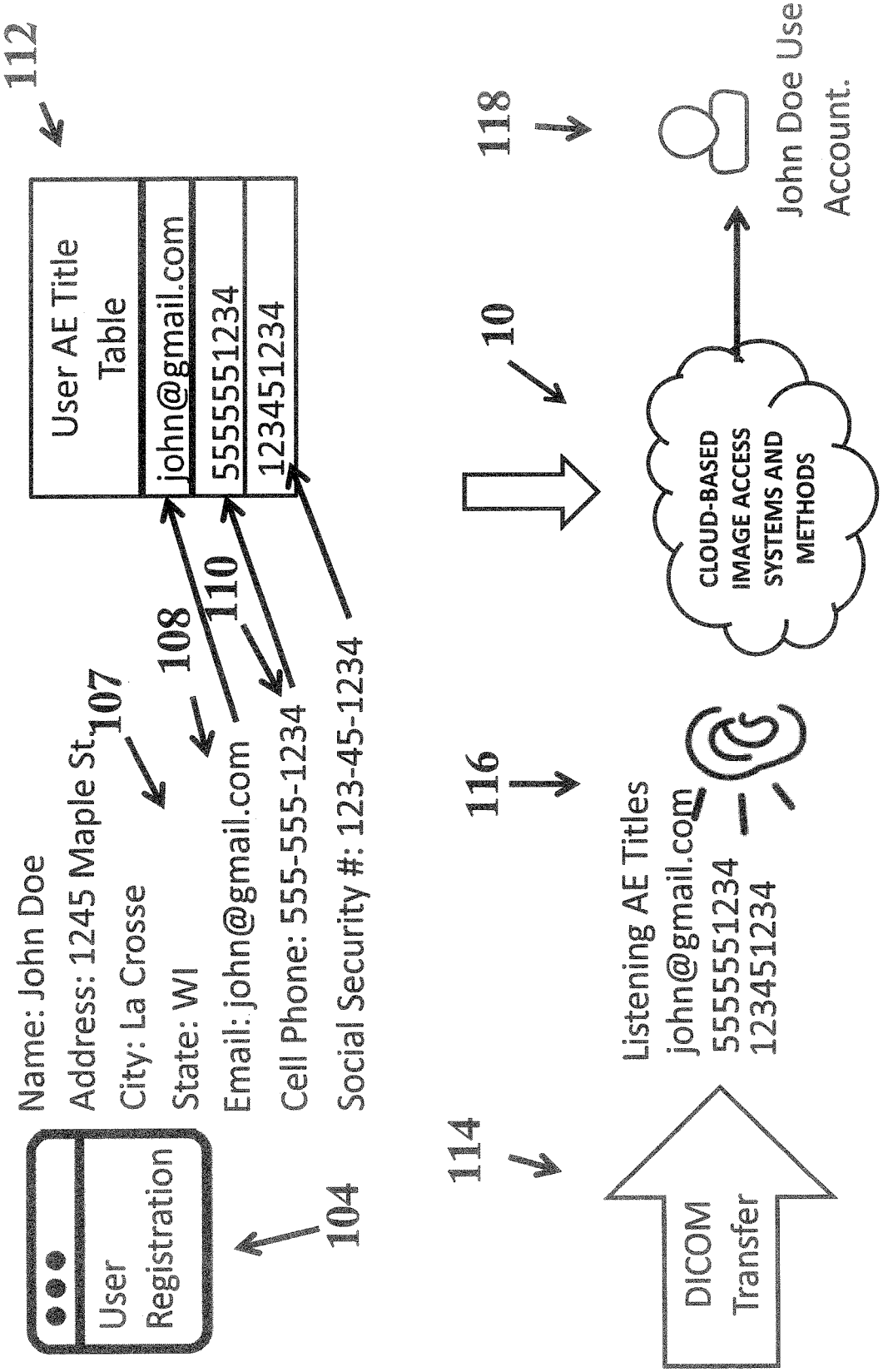
FIG. 5B is an exemplary diagram illustrating an image mapping method of the image access system using personal data to map images to the recipient according to various embodiments.

FIG. 5B illustrates how the solution determines multiple identifiers for users in respect to incoming images over DICOM protocol from an acquisition device or image access system. In the illustration, the image access system identifies Email 107, Cell Phone 108, and Social Security number 110 to be unique to the individual user The system may determine the data to be unique because the database may have unique keys that cannot be associated to multiple accounts which may indicate the data is unique. These data points are entered at the time of registration 104 on the image access system. The new identifiers are stored to the image access system database in a table reserved for AE Titles 112. These entries 112 are used by the system 10 to "listen" 116 for incoming images 114 that have the AE Title with the same characters. The system performs a handshake but only on preconfigured ports with messages that meet the preconfigured AETitle. Existing systems may have a predefined list of AE titles to accept. The improved system may listen for more than just an AE title on a given list. The system may accept the AE title and then compare it to any existing title to determine that it is "new". The characters may be an exact match of the user data or variance of (capitals, symbols, etc) Incoming DICOM files will be stored to the user account 118 that match ANY of the single data points 112. For example, a mobile number may be entered with or without dashes or a leading country code, and the image access will determine the base of the mobile number to use in various embodiments to match an account. This provides the ability for care providers or anyone, who may have a patient's cell phone number, the capability to send images to the specific patient securely. The solution uses a database table of AE Titles, that commonly take the form of, for example, common text, numbers, email address, phone number, or any combination of numbers and letters, to automatically match users to incoming images. A database table may be used to perform the checking for duplicate identifiers at a pace consistent with current communications protocols. For example; if user Jon Doe signs up for the solution and enters his social security as 123-45-6789 (9 digits) and Jane Doe signs up incorrectly with a cell phone number of 123-456-789 (the same 9 digits) the solution may quickly tell Jane Doe that the number entered already exists in the solution. However Jane Doe may use 123-456-7891 (10 digits) as her cell phone and still be a unique identifier.

Figure 5C:
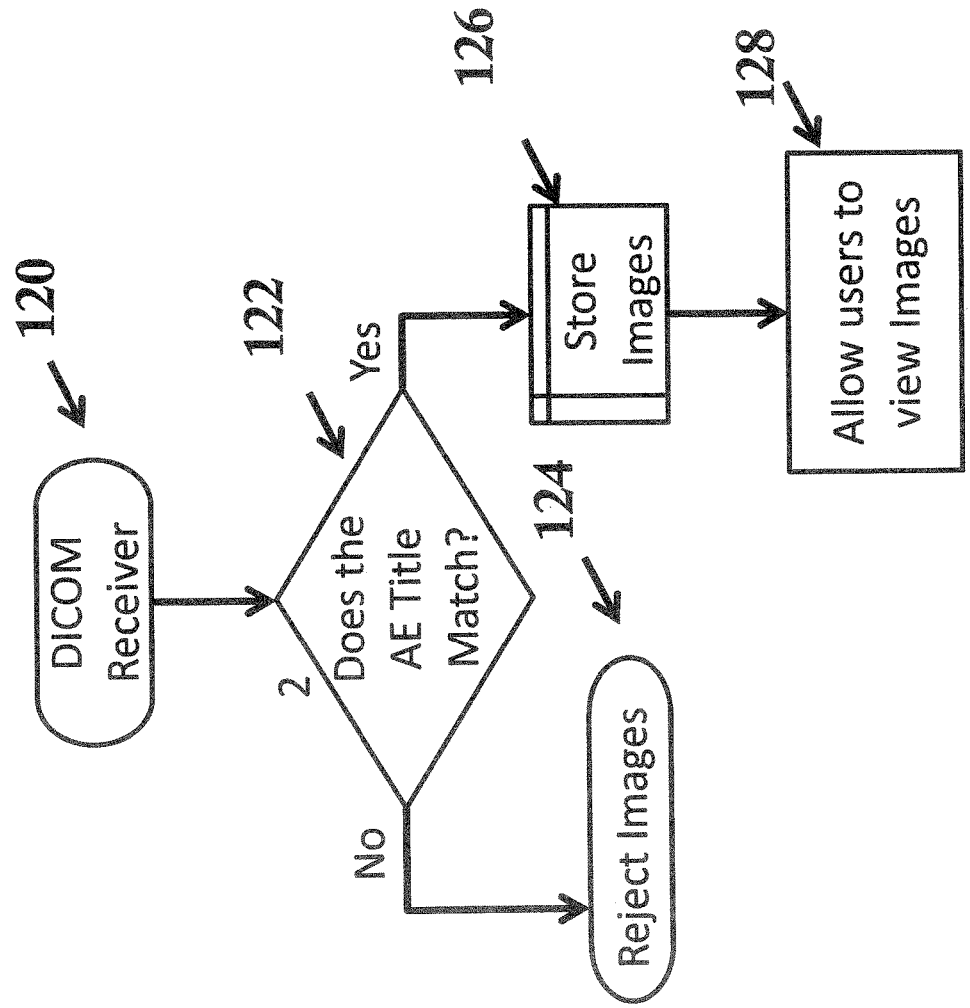
FIG. 5C is an exemplary flow chart illustrating the steps a traditional PACS system process incoming DICOM files to accept or reject images.
Figure 5D:
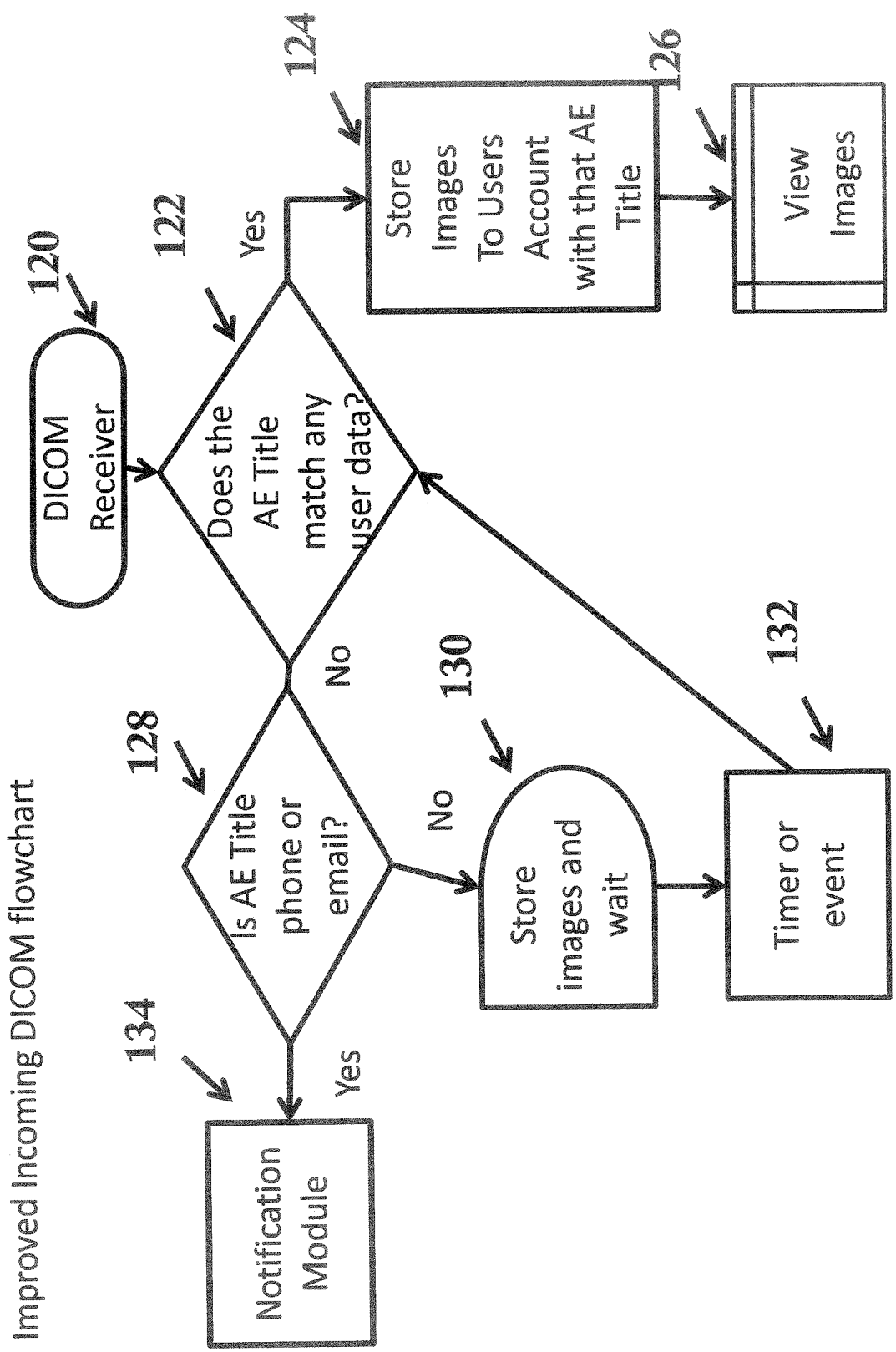
FIG. 5D is an exemplary flow chart illustrating the steps the image access system processes incoming DICOM files according to various embodiments.

FIG. 5C illustrates a comparison of how images are received on a Traditional PACS vs the image access system.

A major drawback of a traditional PACS is that it may reject images with an AE Title that does not match any of the predefined AE Titles. In a traditional PACS, first the DICOM Receiver accepts the incoming connection on the correct IP and port number 120. Following, the DICOM receiver then checks to see if the AE Title, of the incoming images, matches the configuration set in the PACS software 122. The configuration set is normally defined by the software vender and the PACS administrator or between two PACS administrators. This configuration set is predefined and agreed upon by both parties before a successful DICOM transmission can occur. This requires some type of communication outside of the PACS (email, phone call) between both parties in order to agree on the configuration set. If the AE Title does not match, they are rejected and not stored or registered in the database 124. If the AE Title does match, it is stored to the file system and records are created in the database 126. Users are then able to find the images by doing a database query from their client application.

FIG. 5D illustrates an even further improvement of the image access system, over previous PACS, by accepting all images and doing analysis of the AE Title to proactively send notifications to non-registered users. When images are sent from a device or image access system they are received, on the image access system, by the DICOM receiver 120. As in previous illustrations, the receiver determines if the AE Title belongs to a registered user 122 by querying the AE Title Table 112. If a similar match is made, then that system assigns the images to the corresponding user 124 thus allowing for user access to the images 126, as user access to images is controlled by a positive conditional matching status within the database records. If the exact matching AE Title does not already exist in the image access database, the image access system analyzes the characters of the AE Title provided for patterns matching, for example, email or cell phone 128. If the AE Title appears to be a cell phone or email (e.g., based on a serious of logical operators that analyze the characters to determine the format corresponding to an email or cell phone number), the system routes it to the corresponding notification module 134. If the AE Title does not appear to be a cell phone or email: The image access system holds the images and waits 130 for an event 132 (e.g. new user registration or time delay), to query the AE Title table, for matching user data. If no fields match the incoming AE Title 122 the images are held indefinitely. This creates a more resilient solution that doesn't require any registration for the receiving party. The image sender can send images first, using DICOM Protocol, to initiate the workflow. For example: An Imaging Center 16 may acquire patients' images through an acquisition device 12 and DICOM send, to the image access system 10, using the patient's email address. The sending of images can happen immediately even while the patient is in the room. The solution will hold the images until the user registers.

Figure 5E:
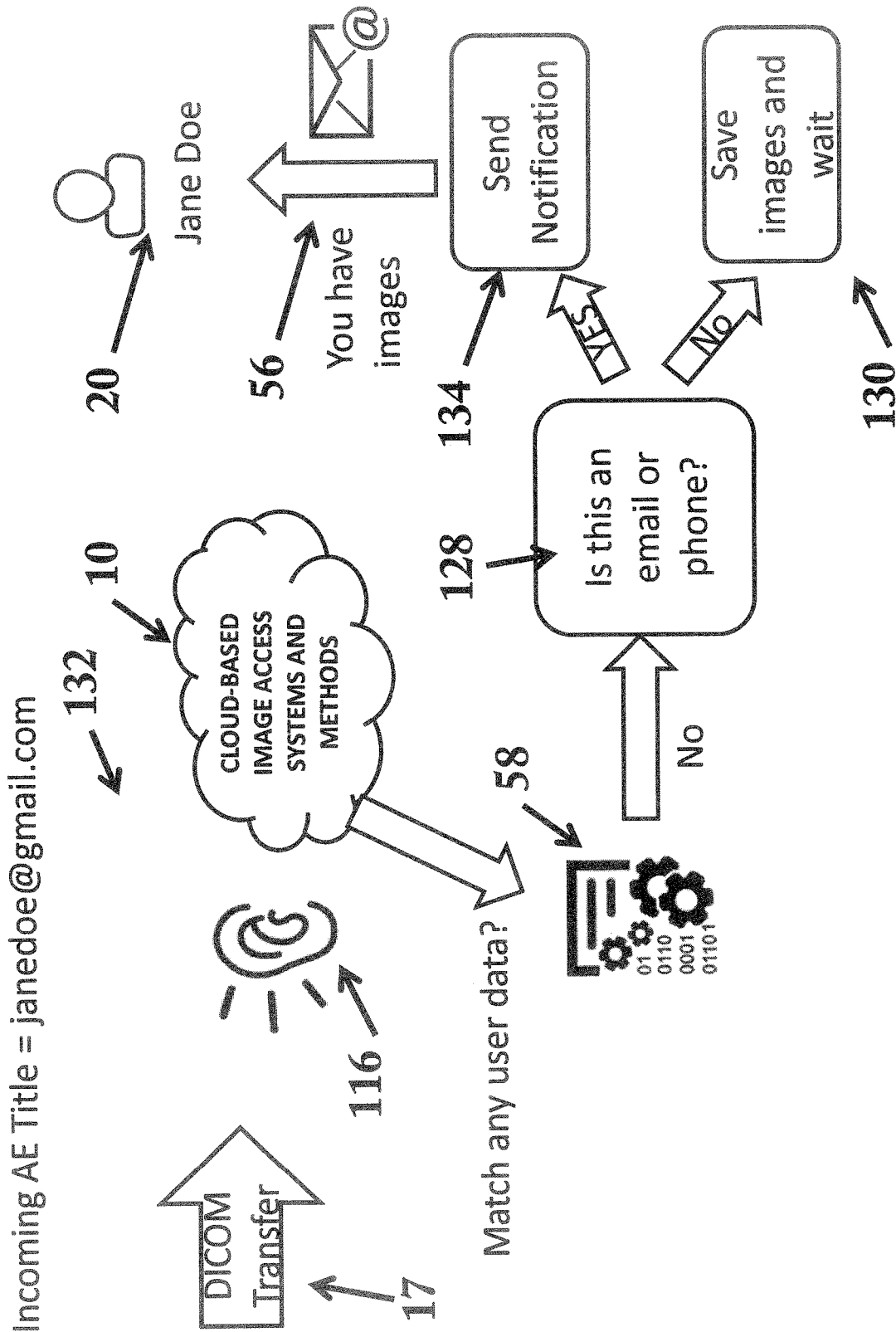
FIG. 5E is an exemplary diagram illustrating how the image access system processes the AE Title for user contact information according to various embodiments.

FIG. 5E is an illustration of how an unregistered patient is able to receive images, using email notification, from an outside source (registered or unregistered) via DICOM protocol. This elaborates slightly on FIG. 5D in that it depicts an additional step of sending an email 56 to the unregistered user 20.

When images are sent from a device or image access system over DICOM protocol 17 they are received, on the image access system 10, by the DICOM receiver 116. As in previous illustrations, the receiver, determines if the AE Title 132 belongs to a registered user 122 by querying the AE Title Table 58. If the AE Title does not exist, the image access system analyzes the characters for patterns matching, for example, email or cell phone 128. If the AE Title 132 does appears to be a cell phone or email, the system routes it to the corresponding notification module 134. In the illustration, the AE title 132 is an email, so communicates with the outgoing mail provider 56 to send a notification to the unregistered user 20. If the AE Title 132 does not appear to be a cell phone or email: The image access system saves the images and waits 130 for an event.

This work flow allows for dramatically easier operation of sending images between two parties with little or no supervision of an image access system Administrator (e.g. someone versed in the operation of PACS)

For example: An Imaging Center 16 may acquire patients' images and DICOM send, to the image access system, using the patient's email address. The sending of images can happen immediately even while the patient is in the room. The image access system will hold the images AND send an email to the patient. It does not require the patient to register prior to the image acquisition appointment.

Figure 6:
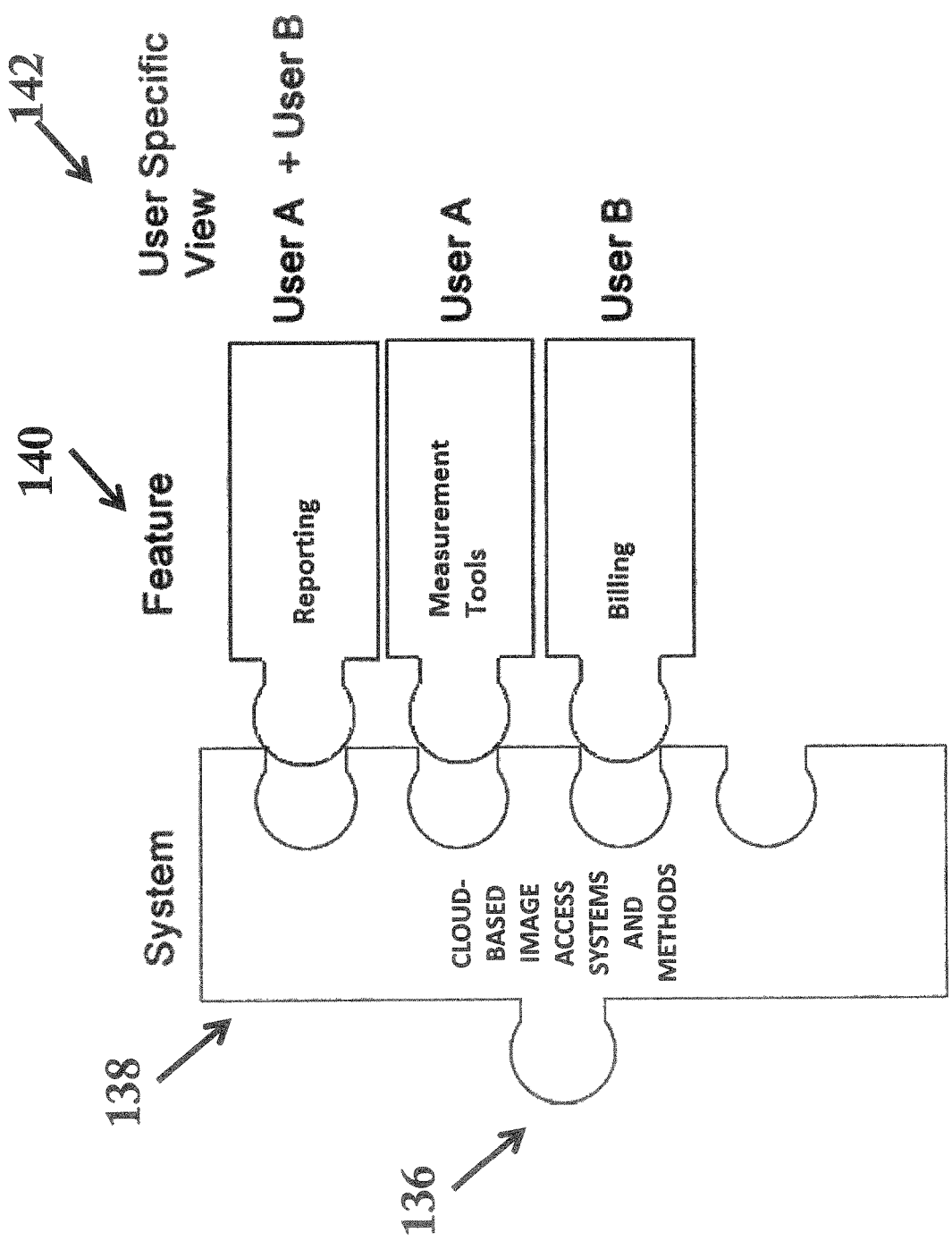
FIG. 6 is an exemplary diagram illustrating (by way of example only) a host of individualized modules which may form part of the image access system and which make it extensible to allow controlled user delivery of features specific for the user's requirements.

FIG. 6 is an illustration of the architecture of the image access system and its utilization, for example, of application programming interfaces (API's) to receive/write data on the server side 136 and dynamically display data to the users client side 142. The image access system has the ability to interface with data sources, for example, Hospital Information System (HIS) and HL7 protocols 136. Features 140 such as reporting, measurement tools, and billing can be generated, on the image access system, to the users specific permissions, needs, or profile type of the user 142. The final output is specific, but not limited to, users requirements, login type, or permissions 142.

For example a Patient might require a different user interface than a Cardiologist. User types are not new to software applications but it is definitely advancement to existing PACS technology. In existing technology, differing types of interface needs are handled by the client application installation. Switching user interfaces often means manually installing another application on the user's computer. By using the browser, in the image access system, to download the viewer 40 and data 42, the interface can be customized each time it is downloaded.

Figure 7:
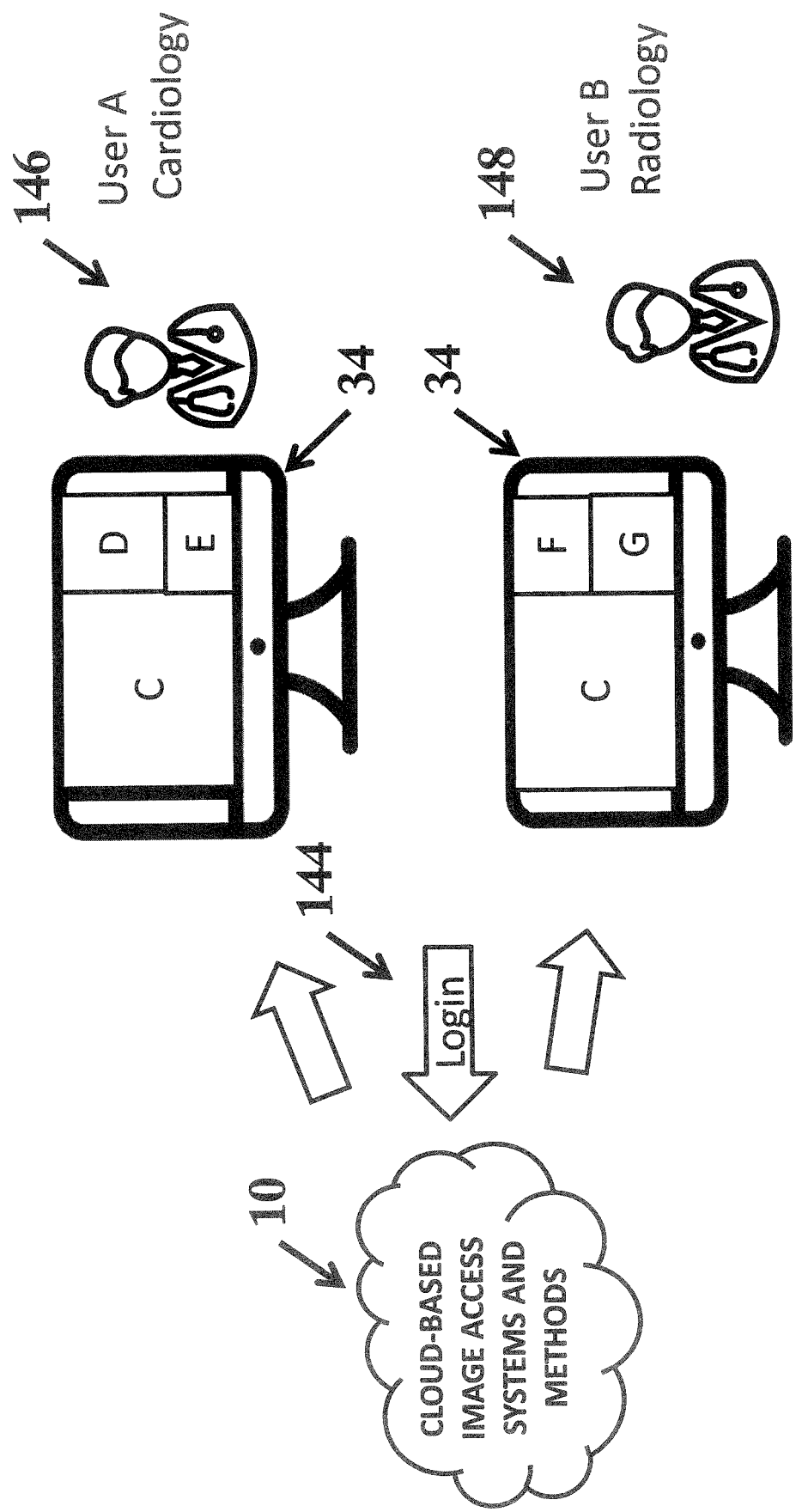
FIG. 7 is an exemplary diagram illustrating the feature of the image access system of providing individualized viewing options based on user login according to various embodiments.

FIG. 7 Further elaborates on FIG. 6 to show the customized display to the user type from the image access system 10. It illustrates visible modules of the application that are rendered on the server, and sent to the users interface, after login 144. The image access system 10 is able to render the interface to the service customized to the users' profile type, login, or permissions.

The customized user interface is presented to the user. In this case a Radiologist (User B) 148 and a Cardiologist (User A) 146. User A and User B require different measurement tools and features 150 & 152.

Figure 8:
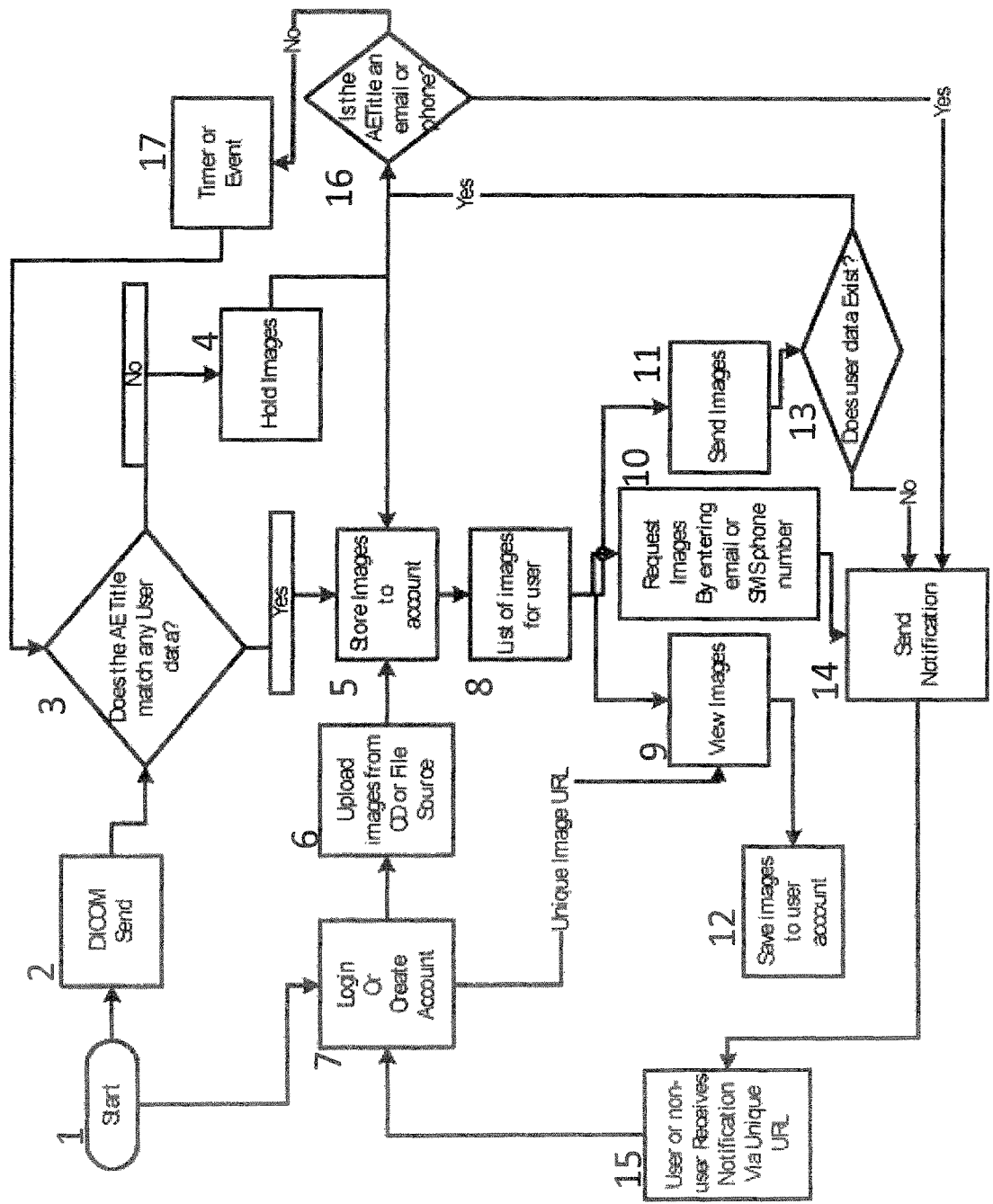
FIG. 8 is an exemplary flow chart illustrating one embodiment of the image access system for delivering and receiving DICOM images according to various embodiments.

FIG. 8 is high level flow chart of, for example, how the various modules and features may be configured together to provide a service for securely sending and receiving DICOM files, notifications, reports, and patient data.

The solution allows two entry points 152 to accommodate unregistered users. The non-registered users use a DICOM send operation to interface with the system. Other types of transfers over https ("sending of image" FIG. 4B, or "request images" FIG. 4A) at least one user is registered to complete the task.

The image access system's key features are, for example, a simplified user interface for finding images quickly through a list (specific to the user) presented to the user through a web interface 154 (FIG. 2A), the ability to view images specific to the user, received from other users 160, the ability to request image from anyone 158 (FIG. 4A), and send images to anyone 156 (FIG. 4B), with little or no administration or communication. The image access system analyzes the incoming AE Title (FIG. 5E) to figure out how to communicate and notify the end user automatically.

Figure 9:
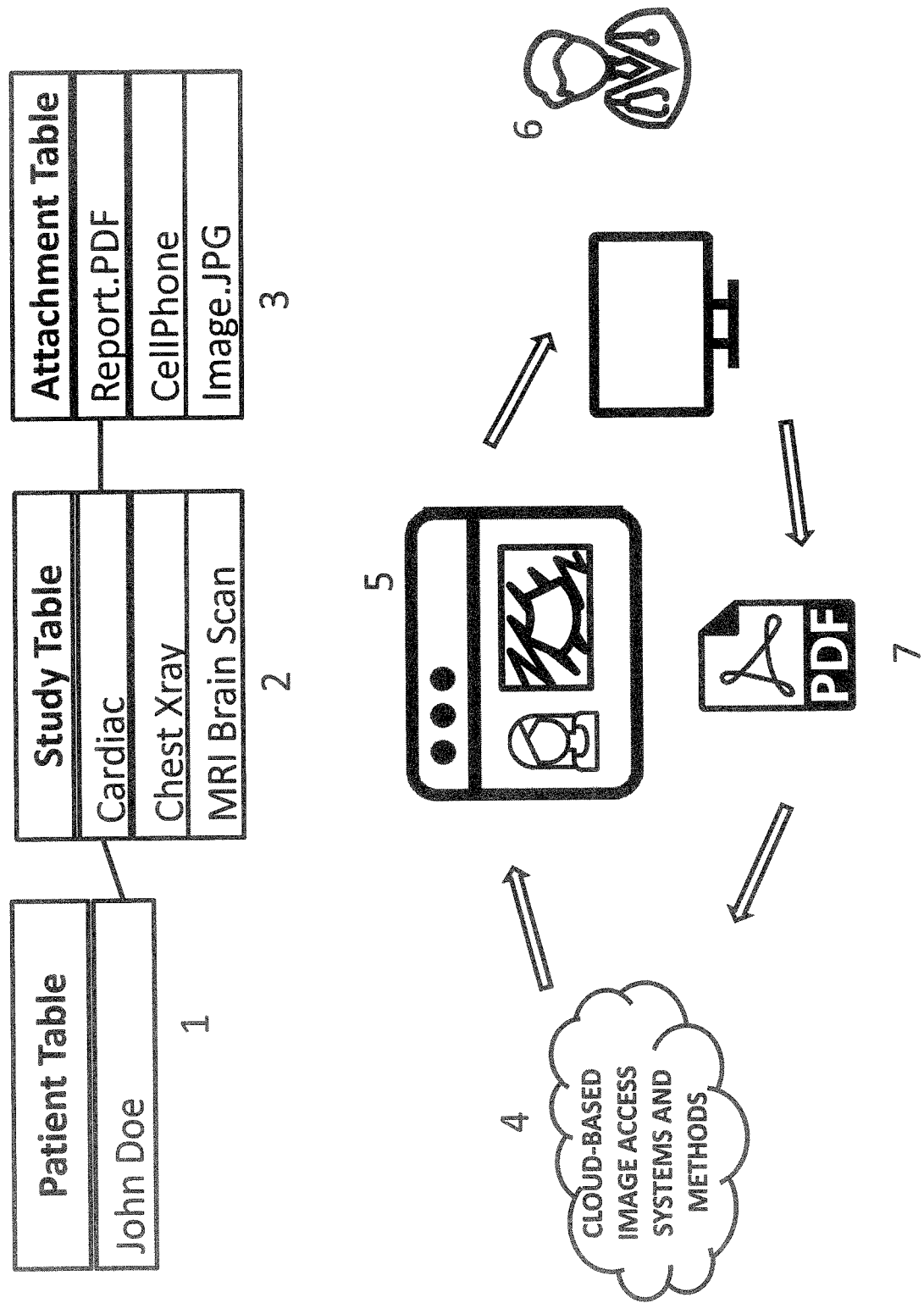
FIG. 9 is an exemplary diagram illustrating the feature of the image access system of storing non-DICOM images to a patient study according to various embodiments.

FIG. 9 is an illustration of the ability to store, and index, non-DICOM related media and files, to an individual study or image in one aspect. This may contain, for example, PDF(s), moving image(s), picture(s), and text. The various aspects include, for example, the patient table 160 were it has a relational database connection (one to one or one to many) to the studies table 162. The studies table may contain list of individual images or collection of images to the patient table 160. The attachment table 164 contains documents or files, pertaining to the select study or images table, in a one to one or one to many relationships in the database. The relationship may also be indexed using non-relational databases (e.g. Mongo DB, and other "No SQL" applications for data processing) The image access system delivers the patient specific study or study specific images to the user via the viewer 40. User is presented with the ability to upload documents, files, and text 166 to the image access System through the interface. The image access's ability to associate uploaded items (e.g., documents, files and text) to a table structure provides greater flexibility in collection and communicating of the combined content of the viewer, images, and associated data. This structure is superior to simple single associations (e.g., as in an email attachment) in that any combination of index or indexes may be used to collect the components for viewing the data and image. This becomes important when non-DICOM information and files needs to be used to make a diagnosis. For example if a patient has a cell phone video of how an injury effects patent movement. This type of observation is usually an observation of a physician or health care worker. The ability to append this data also opens up bi-directional communication between two remote parties such as patient and doctor.

Figure 10:
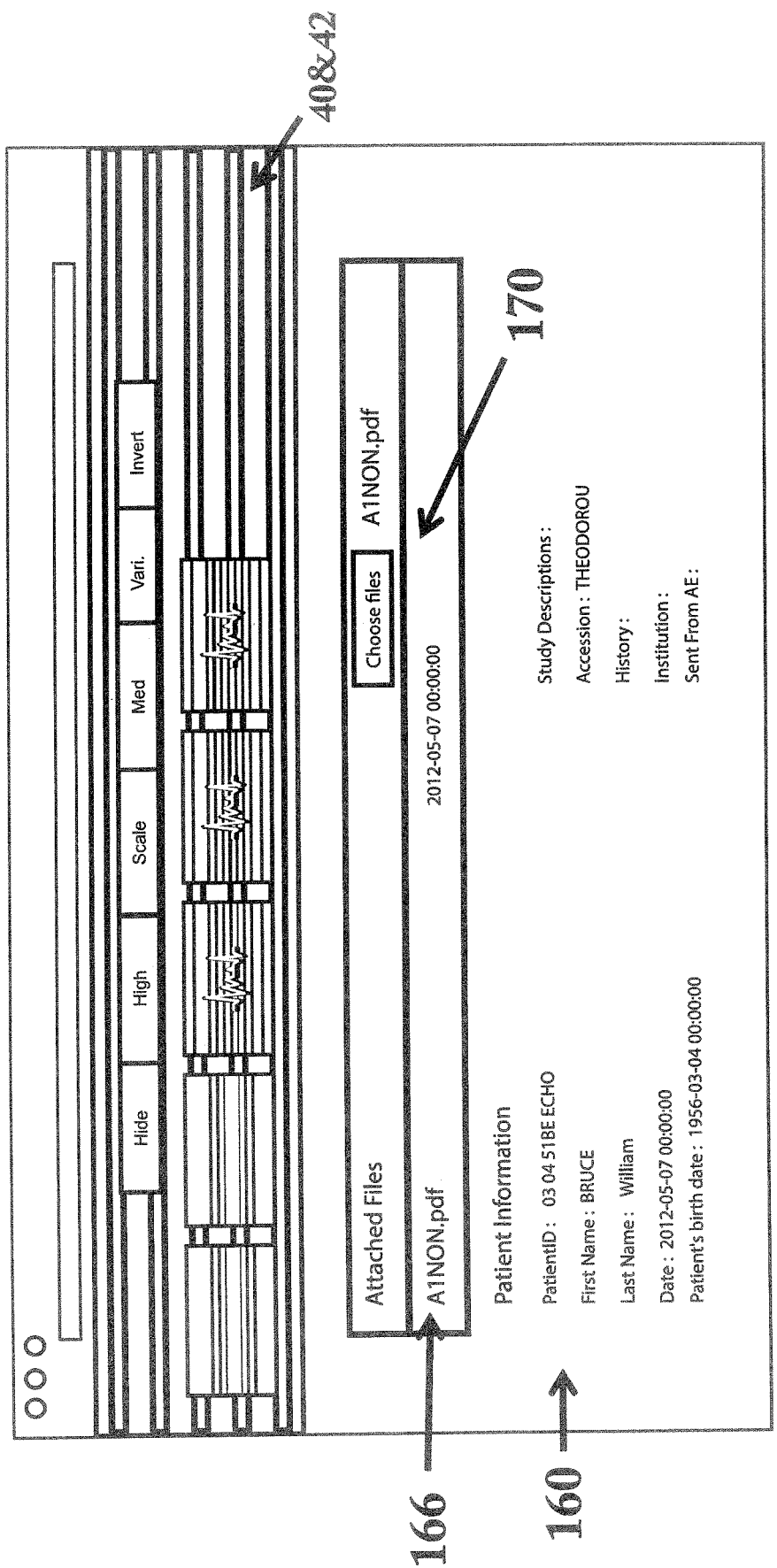
FIG. 10 is a representation of an exemplary solution, illustrating the feature of attaching non-DICOM data to an existing study according to various embodiments.
Figure 11:
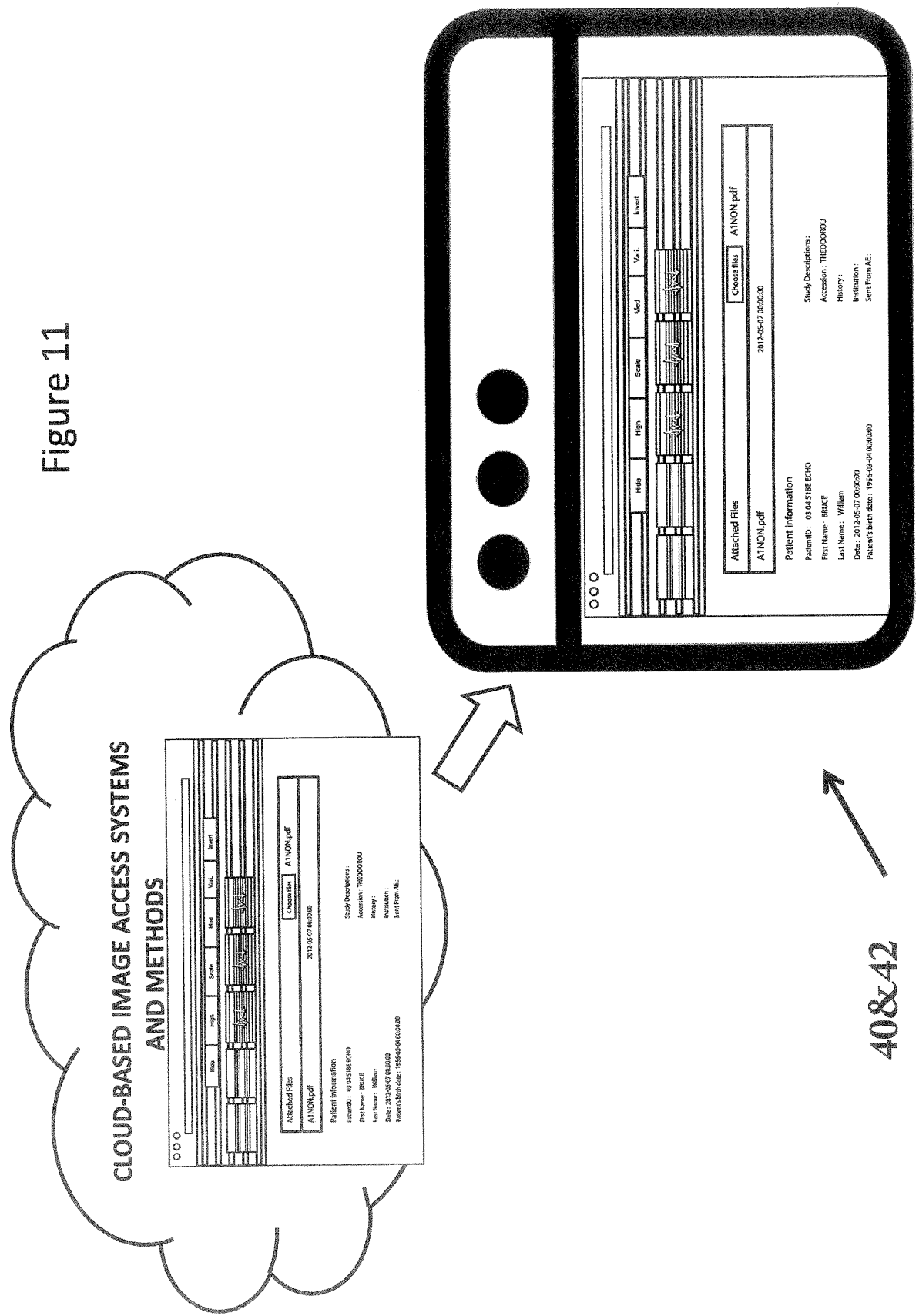
FIG. 11 is a representation of an exemplary solution, illustrating the feature of DICOM and viewer downloaded to the browser according to various embodiments.

FIG. 10 is a representation of the web user interface to the image access system 10. It is one graphical representation of the ability to attach non-DICOM file(s) to a single or multiple DICOM image(s) further described in FIG. 9. The graphical representation is not necessarily limited to, a web interface. The representation demonstrates the relationship to the patient table 160 and the viewing of patient image data 41 and viewer 40. The ability to upload from a user's local computer or device from storage is handled through the "choose file" button 170 were the user must select the file(s) according to various embodiments. By selecting the file(s) the user initiates an upload to the server. The image access system 10 sends the file to storage and writes the location, date, and additional information to the systems database. Then is indexed to, for example, the table(s) image, study, or patient. Any combination of indexing to the image, study, or patient to the attachment may be used. The image access ability to index non-DICOM files to single or multiple DICOM images provides for collecting of all references to the DICOM files and communication of these references, for example access through a unique URL link for viewing. FIG. 11 is a representation of the web user interface to the image access system 10. It is one graphical representation of the ability to send image data, patient data, and DICOM viewer to the browser.

Any of the features or attributes of the above the above described embodiments and variations can be used in combination with any of the other features and attributes of the above described embodiments and variations as desired.

Figure 13:
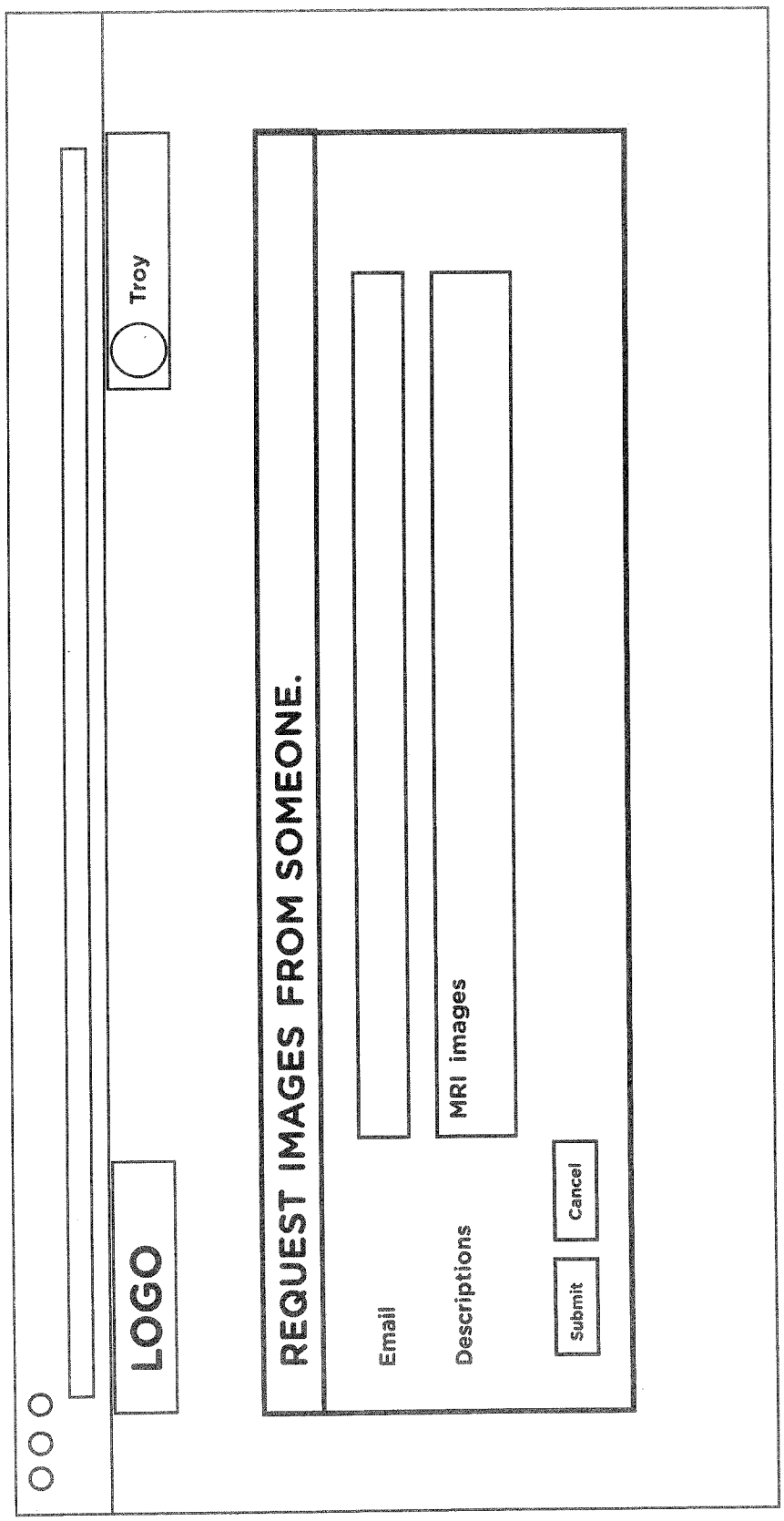
FIG. 13 is a representation of an exemplary solution, illustrating the feature of requesting images from a non-registered user according to various embodiments.
Figure 15:
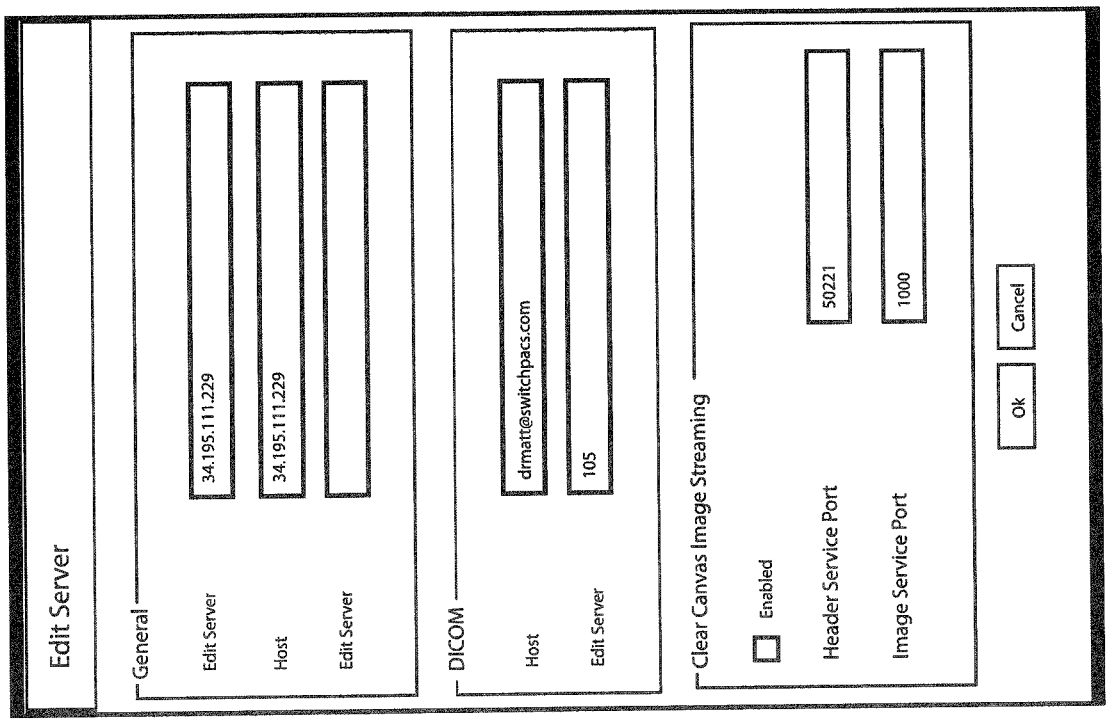
FIG. 15 is a representation of image access software, illustrating the ability to send to the solution by utilizing an email as the AE Title according to various embodiments.
Figure 16:
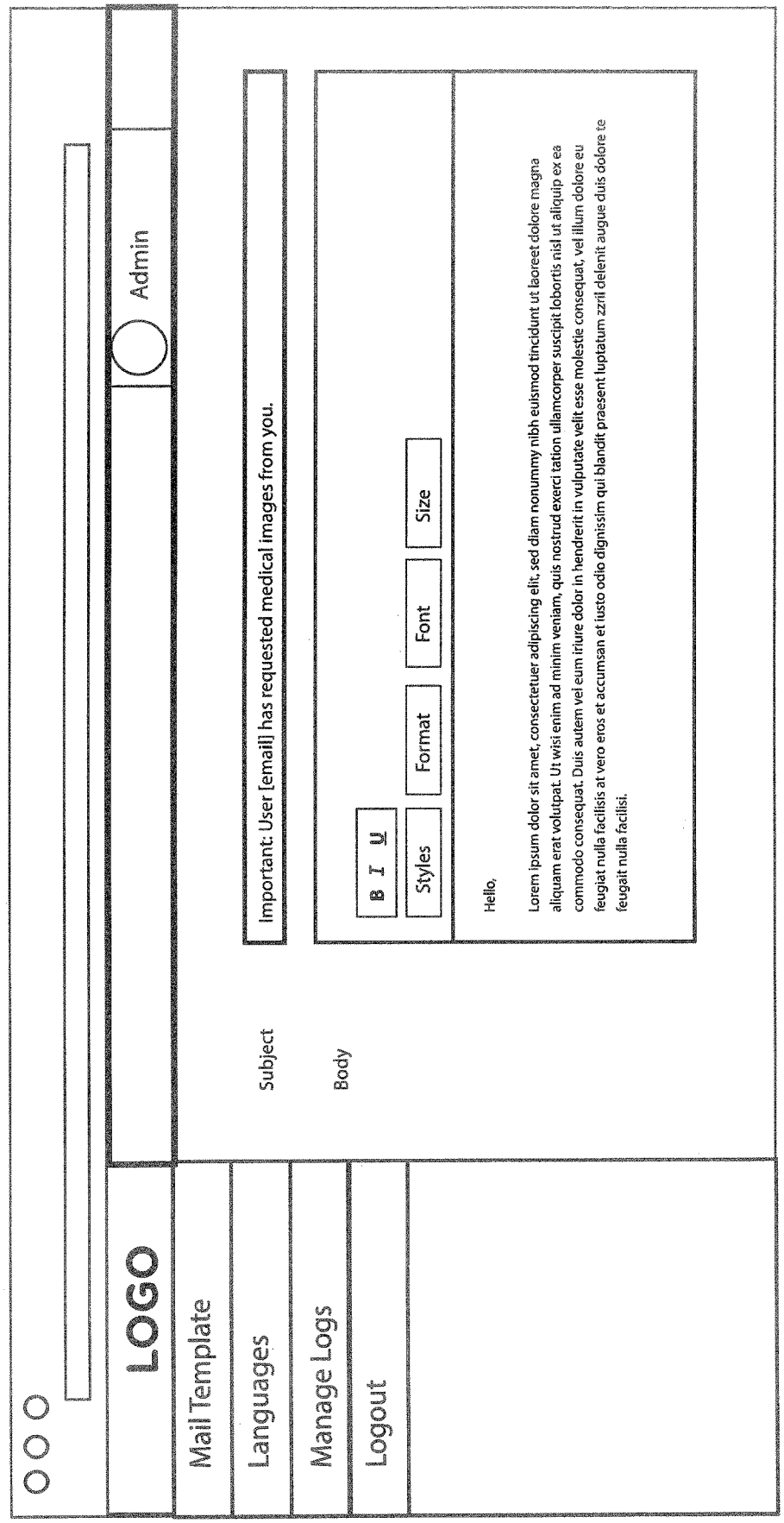
FIG. 16 is a representation of an exemplary solution administration screen, illustrating the feature of dynamic notifications to emails according to various embodiments.
Figure 17:
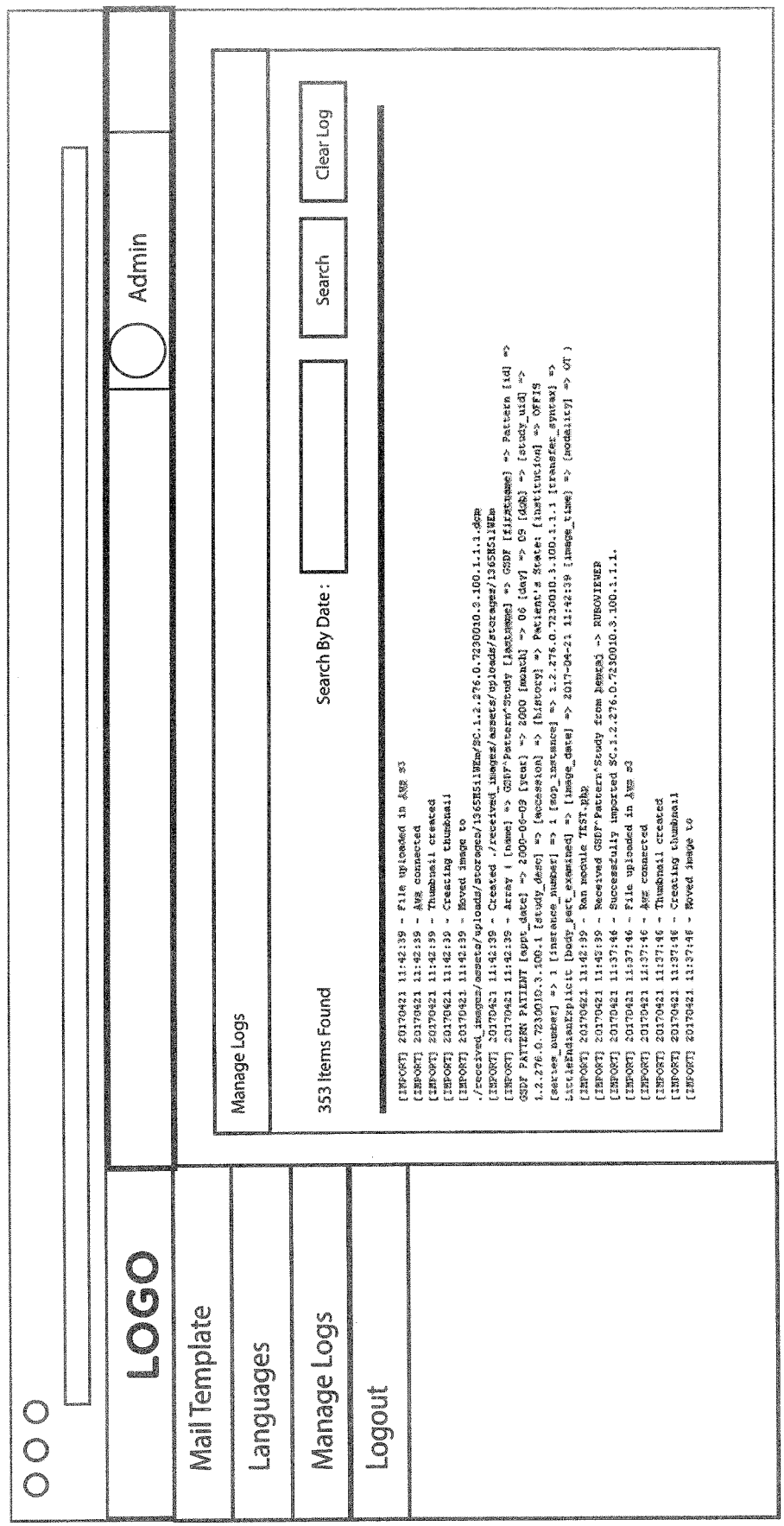
FIG. 17 is a representation of an exemplary solution administration screen, illustrating the log file of incoming studies and how is communicates with third party provider Amazon according to various embodiments.
Figure 18:
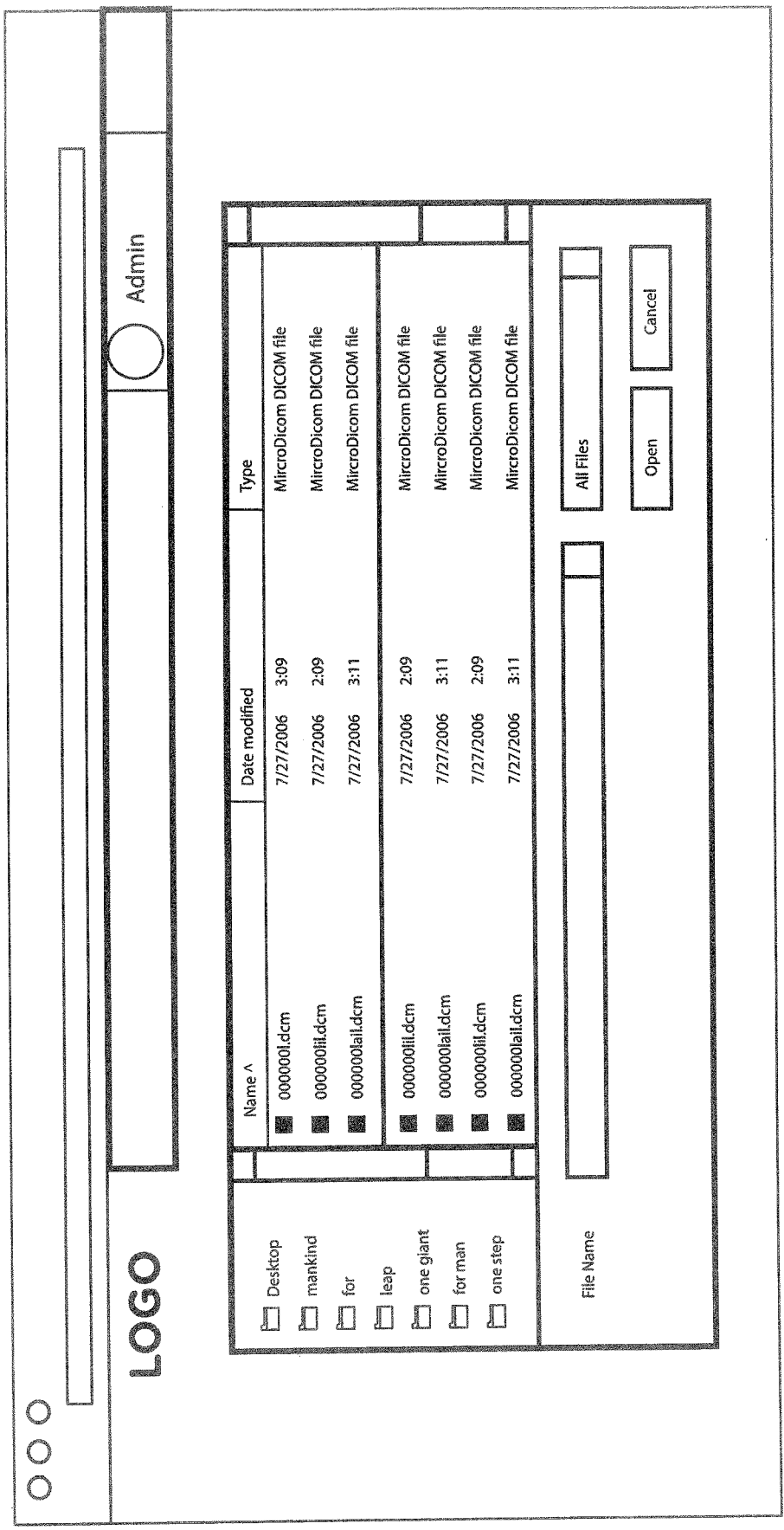
FIG. 18 is a representation of an exemplary solution, illustrating the feature to upload DICOM images by the user according to various embodiments.
Figure 19:
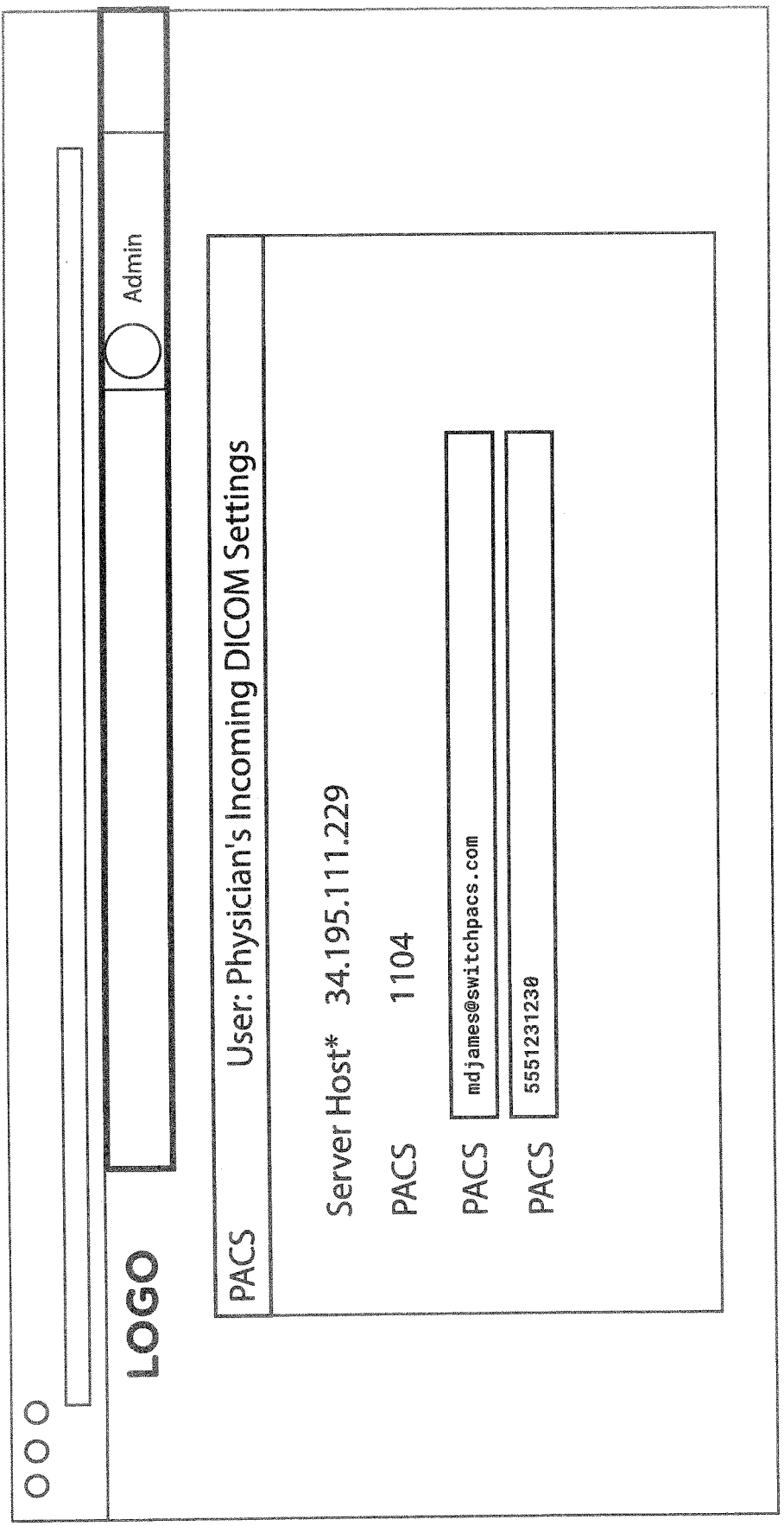
FIG. 19 is a representation of an exemplary solution, illustrating the feature of multiple incoming AE Titles for each user according to various embodiments.

The software of the image access system 10 of the present disclosure may be graphically displayed in any number of suitable manners, including but not limited to the exemplary graphic user interfaces (GUIs) set forth in FIGS. 10-20, with respectively (by way of example only) represent: FIG. 10—GUI representation illustrating the feature of attaching non-DICOM data to an existing study; FIG. 11—GUI representation illustrating the feature of DICOM and viewer downloaded to the browser; FIG. 12—GUI representation illustrating the feature to send multiple images to multiple emails; FIG. 13—GUI representation illustrating the feature of requesting images from a non-registered user; FIG. 14—GUI representation illustrating the feature to send a study to an email; FIG. 15—GUI representation illustrating the ability to send to the solution by utilizing an email as the AE Title; FIG. 16—GUI representation illustrating the feature of dynamic notifications to emails; FIG. 17—GUI representation illustrating the log file of incoming studies and how is communicates with third party provider Amazon; FIG. 18—GUI representation illustrating the feature to upload DICOM images by the user; FIG. 19—GUI representation illustrating the feature of multiple incoming AE Titles for each user; and FIG. 20—GUI representation illustrating the menu and work list of studies.

Figure 21:
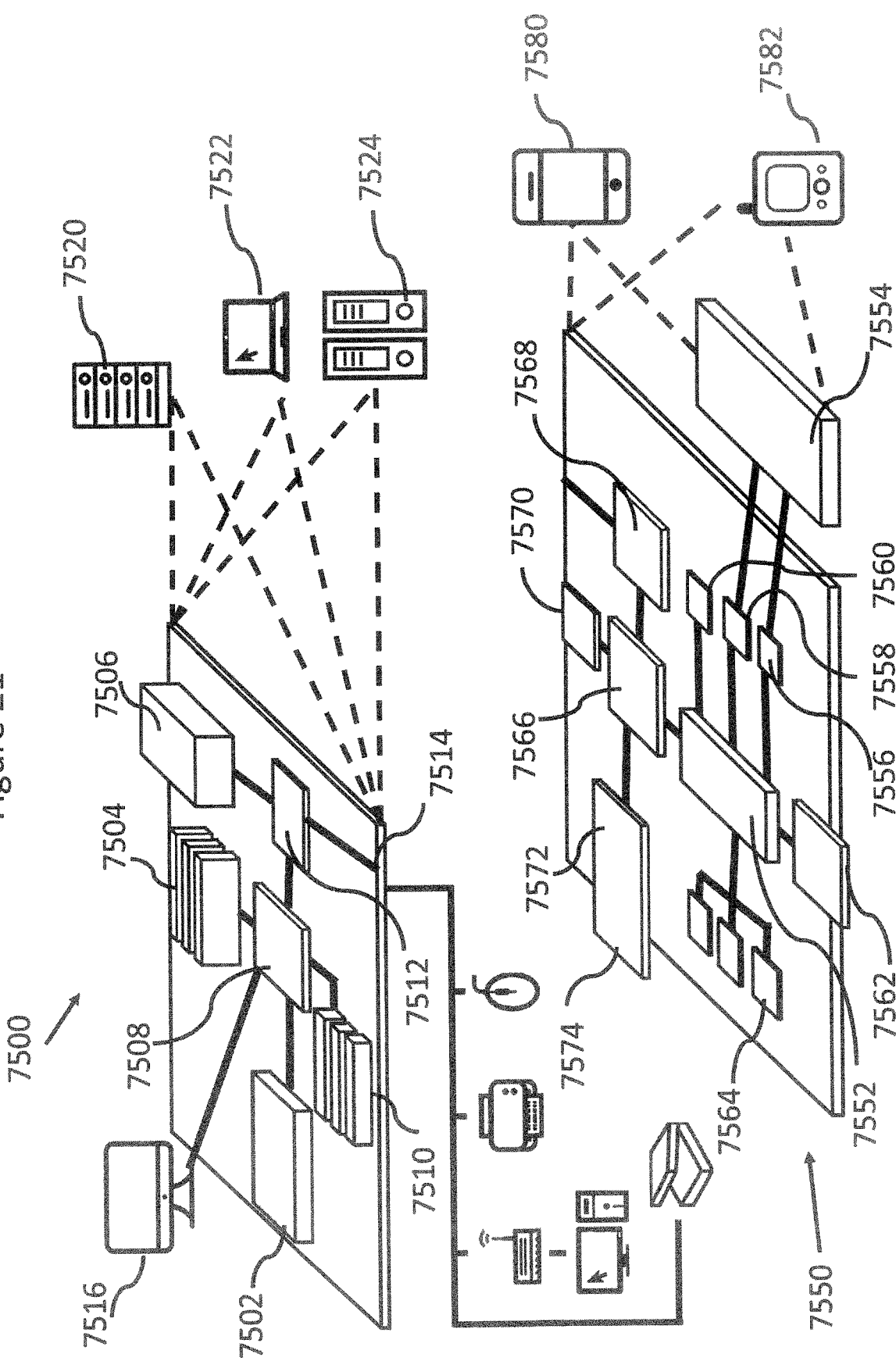
FIG. 21 is a block diagram of exemplary computer systems forming part of the image access system according to various embodiments.

FIG. 21 is a block diagram of computing devices 7500, 7550 that may be used to implement the systems and methods described in this document, as either a client or as a server or plurality of servers. Computing device 7500 is intended to represent various forms of digital computers, such as laptops, desktops, workstations, personal digital assistants, servers, blade servers, mainframes, and other appropriate computers. Computing device 7550 is intended to represent various forms of mobile devices, such as personal digital assistants, cellular telephones, smartphones, and other similar computing devices. In this example, computing device 7550 may represent electronic device 17, while computing device 7500 may represent computing systems that serve as the "cloud" referenced in this disclosure. The components shown here, their connections and relationships, and their functions, are meant to be examples only, and are not meant to limit implementations described and/or claimed in this document.

Computing device 7500 includes a processor 7502, memory 7504, a storage device 7506, a high-speed interface 7508 connecting to memory 7504 and high-speed expansion ports 7510, and a low speed interface 7512 connecting to low speed bus 7514 and storage device 7506. Each of the components 7502, 7504, 7506, 7508, 7510, and 7512, are interconnected using various busses, and may be mounted on a common motherboard or in other manners as appropriate. The processor 7502 can process instructions for execution within the computing device 7500, including instructions stored in the memory 7504 or on the storage device 7506 to display graphical information for a GUI on an external input/output device, such as display 7516 coupled to high-speed interface 7508. In other implementations, multiple processors and/or multiple buses may be used, as appropriate, along with multiple memories and types of memory. Also, multiple computing devices 7500 may be connected, with each device providing portions of the necessary operations (e.g., as a server bank, a group of blade servers, or a multi-processor system).

The memory 7504 stores information within the computing device 7500. In one implementation, the memory 7504 is a volatile memory unit or units. In another implementation, the memory 7504 is a non-volatile memory unit or units. The memory 7504 may also be another form of computer-readable medium, such as a magnetic or optical disk.

The storage device 7506 is capable of providing mass storage for the computing device 7500. In one implementation, the storage device 7506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 7504, the storage device 7506, or memory on processor 7502.

The high-speed controller 7508 manages bandwidth-intensive operations for the computing device 7500, while the low speed controller 7512 manages lower bandwidth-intensive operations. Such allocation of functions is by way of example only. In one implementation, the high-speed controller 7508 is coupled to memory 7504, display 7516 (e.g., through a graphics processor or accelerator), and to high-speed expansion ports 7510, which may accept various expansion cards (not shown). In the implementation, low-speed controller 7512 is coupled to storage device 7506 and low-speed expansion port 7514. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 7500 may be implemented in a number of different forms, as shown in the figure. For example, it may be implemented as a standard server 7520, or multiple times in a group of such servers. It may also be implemented as part of a rack server system 7524. In addition, it may be implemented in a personal computer such as a laptop computer 7522. Alternatively, components from computing device 7500 may be combined with other components in a mobile device (not shown), such as device 7550. Each of such devices may contain one or more of computing device 7500, 7550, and an entire system may be made up of multiple computing devices 7500, 7550 communicating with each other.

Computing device 7550 includes a processor 7552, memory 7564, an input/output device such as a display 7554, a communication interface 7566, and a transceiver 7568, among other components. The device 7550 may also be provided with a storage device, such as a microdrive or other device, to provide additional storage. Each of the components 7550, 7552, 7564, 7554, 7566, and 7568, are interconnected using various buses, and several of the components may be mounted on a common motherboard or in other manners as appropriate.

The processor 7552 can execute instructions within the computing device 7550, including instructions stored in the memory 7564. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 7550, such as control of user interfaces, applications run by device 7550, and wireless communication by device 7550.

Processor 7552 may communicate with a user through control interface 7558 and display interface 7556 coupled to a display 7554. The display 7554 may be, for example, a TFT (Thin-Film-Transistor Liquid Crystal Display) display or an OLED (Organic Light Emitting Diode) display, or other appropriate display technology. The display interface 7556 may comprise appropriate circuitry for driving the display 7554 to present graphical and other information to a user. The control interface 7558 may receive commands from a user and convert them for submission to the processor 7552. In addition, an external interface 7562 may be provided in communication with processor 7552, so as to enable near area communication of device 7550 with other devices. External interface 7562 may provide, for example, for wired communication in some implementations, or for wireless communication in other implementations, and multiple interfaces may also be used.

The memory 7564 stores information within the computing device 7550. The memory 7564 can be implemented as one or more of a computer-readable medium or media, a volatile memory unit or units, or a non-volatile memory unit or units. Expansion memory 7574 may also be provided and connected to device 7550 through expansion interface 7572, which may include, for example, a SIMM (Single In Line Memory Module) card interface. Such expansion memory 7574 may provide extra storage space for device 7550, or may also store applications or other information for device 7550. Specifically, expansion memory 7574 may include instructions to carry out or supplement the processes described above, and may include secure information also. Thus, for example, expansion memory 7574 may be provided as a security module for device 7550, and may be programmed with instructions that permit secure use of device 7550. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, cause performance of one or more methods, such as those described above. The information carrier is a computer- or machine-readable medium, such as the memory 7564, expansion memory 7574, or memory on processor 7552 that may be received, for example, over transceiver 7568 or external interface 7562.

Device 7550 may communicate wirelessly through communication interface 7566, which may include digital signal processing circuitry where necessary. Communication interface 7566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 7568. In addition, short-range communication may occur, such as using a Bluetooth, WiFi, or other such transceiver (not shown). In addition, GPS (Global Positioning System) receiver module 7570 may provide additional navigation- and location-related wireless data to device 7550, which may be used as appropriate by applications running on device 7550.

Device 7550 may also communicate audibly using audio codec 7560, which may receive spoken information from a user and convert it to usable digital information. Audio codec 7560 may likewise generate audible sound for a user, such as through a speaker, e.g., in a handset of device 7550. Such sound may include sound from voice telephone calls, may include recorded sound (e.g., voice messages, music files, etc.) and may also include sound generated by applications operating on device 7550.

The computing device 7550 may be implemented in a number of different forms, some of which are shown in the figure. For example, it may be implemented as a cellular telephone 7580. It may also be implemented as part of a smartphone 7582, personal digital assistant, or other similar mobile device.

Additionally computing device 7500 or 7550 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While the inventive features described herein have been described in terms of a preferred embodiment for achieving the objectives, it will be appreciated by those skilled in the art that variations may be accomplished in view of these teachings without deviating from the spirit or scope of the disclosure. Furthermore, the various features of the disclosure have been described using several example embodiments. It should be understood that any feature or combination of features described with regard to a particular example embodiment may be applied to any other example embodiment in any combination without reservation.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy," "meet," "match," "associated with", or similar phrases may include an identical match, a partial match, meeting certain criteria, matching a subset of data, a correlation, satisfying certain criteria, a correspondence, an association, an algorithmic relationship, and/or the like. Similarly, as used herein, "authenticate" or similar terms may include an exact authentication, a partial authentication, authenticating a subset of data, a correspondence, satisfying certain criteria, an association, an algorithmic relationship, and/or the like.

Terms and phrases similar to "associate" and/or "associating" may include tagging, flagging, correlating, using a look-up table or any other method or system for indicating or creating a relationship between elements, such as, for example, (i) a transaction account and (ii) an item (e.g., offer, reward, discount) and/or digital channel. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input, and/or any other method known in the art.

As used herein, "transmit" may include sending electronic data from one system component to another over a network connection. Additionally, as used herein, "data" may include encompassing information such as commands, queries, files, data for storage, and the like in digital or any other form.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein. See, for example, DILIP NAIK, INTERNET STANDARDS AND PROTOCOLS (1998); JAVA® 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at www.csrc.nist.gov/publications/nistpubs/800-145/SP800-145 (last visited June 2012), which is hereby incorporated by reference in its entirety.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware state machine so as to perform the functions described herein will be apparent to persons skilled in the relevant art(s).

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

In various embodiments, components, modules, and/or engines of system 100 may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise in any number of configurations including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

In various embodiments, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEB SPHERE® MQ™ (formerly MQSeries) by IBM®, Inc. (Armonk, N.Y.) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations or any of the operations may be conducted or enhanced by artificial intelligence (AI) or machine learning. Artificial intelligence may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the server may include application servers (e.g. WEBSPHERE®, WEBLOGIC®, JBOSS®, POSTGRES PLUS ADVANCED SERVER®, etc.). In various embodiments, the server may include web servers (e.g. Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE® CHROME® software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Encryption may be performed by way of any of the techniques now available in the art or which may become available—e.g., Twofish, RSA, El Gamal, Schorr signature, DSA, PGP, PKI, GPG (GnuPG), HPE Format-Preserving Encryption (FPE), Voltage, Triple DES, Blowfish, AES, MD5, HMAC, IDEA, RC6, and symmetric and asymmetric cryptosystems. The systems and methods may also incorporate SHA series cryptographic methods, elliptic curve cryptography (e.g., ECC, ECDH, ECDSA, etc.), and/or other post-quantum cryptography algorithms under development.

The firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the internet. A firewall may be integrated as software within an internet server, any other application server components or may reside within another computing device or may take the form of a standalone hardware component.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, N.Y.), various database products available from ORACLE® Corporation (Redwood Shores, Calif.), MICROSOFT ACCESS® or MICROSOFT SQL SERVER® by MICROSOFT® Corporation (Redmond, Wash.), MYSQL® by MySQL AB (Uppsala, Sweden), MONGODB®, Redis, APACHE CASSANDRA®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored, may be provided by an third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data but instead the appropriate action may be taken by providing to the user at the standalone device, the appropriate option for the action to be taken. The system may contemplate a data storage arrangement wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

Distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

Any database discussed herein may comprise a distributed ledger maintained by a plurality of computing devices (e.g., nodes) over a peer-to-peer network. Each computing device maintains a copy and/or partial copy of the distributed ledger and communicates with one or more other computing devices in the network to validate and write data to the distributed ledger. The distributed ledger may use features and functionality of blockchain technology, including, for example, consensus based validation, immutability, and cryptographically chained blocks of data. The blockchain may comprise a ledger of interconnected blocks containing data. The blockchain may provide enhanced security because each block may hold individual transactions and the results of any blockchain executables. Each block may link to the previous block and may include a timestamp. Blocks may be linked because each block may include the hash of the prior block in the blockchain. The linked blocks form a chain, with only one successor block allowed to link to one other predecessor block for a single chain. Forks may be possible where divergent chains are established from a previously uniform blockchain, though typically only one of the divergent chains will be maintained as the consensus chain. In various embodiments, the blockchain may implement smart contracts that enforce data workflows in a decentralized manner. The system may also include applications deployed on user devices such as, for example, computers, tablets, smartphones, Internet of Things devices ("IoT" devices), etc. The applications may communicate with the blockchain (e.g., directly or via a blockchain node) to transmit and retrieve data. In various embodiments, a governing organization or consortium may control access to data stored on the blockchain. Registration with the managing organization(s) may enable participation in the blockchain network.

Data transfers performed through the blockchain-based system may propagate to the connected peers within the blockchain network within a duration that may be determined by the block creation time of the specific blockchain technology implemented. For example, on an ETHEREUM®-based network, a new data entry may become available within about 13-20 seconds as of the writing. On a HYPERLEDGER® Fabric 1.0 based platform, the duration is driven by the specific consensus algorithm that is chosen, and may be performed within seconds. In that respect, propagation times in the system may be improved compared to existing systems, and implementation costs and time to market may also be drastically reduced. The system also offers increased security at least partially due to the immutable nature of data that is stored in the blockchain, reducing the probability of tampering with various data inputs and outputs. Moreover, the system may also offer increased security of data by performing cryptographic processes on the data prior to storing the data on the blockchain. Therefore, by transmitting, storing, and accessing data using the system described herein, the security of the data is improved, which decreases the risk of the computer or network from being compromised.

In various embodiments, the system may also reduce database synchronization errors by providing a common data structure, thus at least partially improving the integrity of stored data. The system also offers increased reliability and fault tolerance over traditional databases (e.g., relational databases, distributed databases, etc.) as each node operates with a full copy of the stored data, thus at least partially reducing downtime due to localized network outages and hardware failures. The system may also increase the reliability of data transfers in a network environment having reliable and unreliable peers, as each node broadcasts messages to all connected peers, and, as each block comprises a link to a previous block, a node may quickly detect a missing block and propagate a request for the missing block to the other nodes in the blockchain network.

Any communication, transmission, and/or channel discussed herein may include any system or method for delivering content (e.g. data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word™ or EXCEL®, an ADOBE® Portable Document Format (PDF) document, etc.), an "ebook," an "emagazine," an application or microapplication (as described herein), an SMS or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network, and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A method comprising:
receiving, by a processor using the Digital Imaging and Communication in Medicine (DICOM) protocol, content from an IP address;
storing, by the processor, the content in association with a sender identifier, in response to the sender being unknown;
receiving, by the processor, a registration for the sender identifier, subsequent to the receiving the content and the storing the content; and
transferring, by the processor using the DICOM protocol, the content to an account associated with the sender identifier, in response to the receiving the registration for the sender identifier.

2. The method of claim 1, wherein the content is a medical image.

3. The method of claim 1, wherein the content is a medical image that is only viewable with DICOM viewer code.

4. The method of claim 1, further comprising receiving, by the processor, the IP address.

5. The method of claim 1, further comprising receiving, by the processor, a port number.

6. The method of claim 1, further comprising receiving, by the processor, the sender identifier.

7. The method of claim 1, further comprising establishing, by the processor, a connection based on the IP address.

8. The method of claim 1, further comprising establishing, by the processor, a connection based on a port number.

9. The method of claim 1, wherein the sender identifier is unknown based on the sender identifier not being within a table of sender identifiers.

10. The method of claim 1, further comprising comparing, by the processor, the sender identifier with a table of sender identifiers.

11. The method of claim 1, wherein the sender identifier is at least one of an Application Entity Title (AE Title), a sender email address, sender cell phone number or a sender social security number.

12. The method of claim 1, wherein communications to overcome firewall and security settings are not needed, prior to receiving the registration.

13. An image access system comprising:
a processor; and
a tangible, non-transitory memory configured to communicate with the processor,
the tangible, non-transitory memory having instructions stored thereon that, in response to execution by the processor, cause the processor to perform operations comprising:
receiving, by the processor using the Digital Imaging and Communication in Medicine (DICOM) protocol, content from an IP address;
storing, by the processor, the content in association with a sender identifier, in response to the sender being unknown;
receiving, by the processor, a registration for the sender identifier, subsequent to the receiving the content and the storing the content; and
transferring, by the processor using the DICOM protocol, the content to an account associated with the sender identifier, in response to the receiving the registration for the sender identifier.

14. The system of claim 13, further comprising receiving, by the processor, the sender identifier.

15. The system of claim 13, further comprising establishing, by the processor, a connection based on the IP address.

16. The system of claim 13, further comprising establishing, by the processor, a connection based on a port number.

17. The system of claim 13, wherein the sender identifier is unknown based on the sender identifier not being within a table of sender identifiers.

18. The system of claim 13, further comprising comparing, by the processor, the sender identifier with a table of sender identifiers.

19. The system of claim 13, wherein the sender identifier is at least one of an Application Entity Title (AE Title), a sender email address, sender cell phone number or a sender social security number.

20. An article of manufacture including a non-transitory, tangible computer readable storage medium having instructions stored thereon that, in response to execution by a processor, cause the processor to perform operations comprising:

- receiving, by the processor using the Digital Imaging and Communication in Medicine (DICOM) protocol, content from an IP address;
- storing, by the processor, the content in association with a sender identifier, in response to the sender being unknown;
- receiving, by the processor, a registration for the sender identifier, subsequent to the receiving the content and the storing the content; and
- transferring, by the processor using the DICOM protocol, the content to an account associated with the sender identifier, in response to the receiving the registration for the sender identifier.

\* \* \* \* \*